(12) United States Patent
Saitoh et al.

(10) Patent No.: US 8,026,664 B2
(45) Date of Patent: Sep. 27, 2011

(54) COMPOUND AND ORGANIC LIGHT EMITTING DEVICE

(75) Inventors: Akihito Saitoh, Yokohama (JP); Keiji Okinaka, Kawasaki (JP); Satoshi Igawa, Fujisawa (JP); Jun Kamatani, Tokyo (JP); Naoki Yamada, Inagi (JP); Masashi Hashimoto, Tokyo (JP); Masanori Muratsubaki, Hachioji (JP); Takao Takiguchi, Chofu (JP); Akihiro Senoo, Kawasaki (JP); Shinjiro Okada, Kamakura (JP); Minako Nakasu, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 760 days.

(21) Appl. No.: 11/912,710

(22) PCT Filed: Apr. 19, 2007

(86) PCT No.: PCT/JP2007/058992
§ 371 (c)(1),
(2), (4) Date: Oct. 26, 2007

(87) PCT Pub. No.: WO2007/123256
PCT Pub. Date: Nov. 1, 2007

(65) Prior Publication Data
US 2009/0033210 A1  Feb. 5, 2009

(30) Foreign Application Priority Data

Apr. 20, 2006  (JP) .................... 2006-116903
Feb. 21, 2007  (JP) .................... 2007-040901

(51) Int. Cl.
*H01L 51/54* (2006.01)
*C09K 11/06* (2006.01)

(52) U.S. Cl. ... 313/504; 313/506; 257/40; 257/E51.049; 428/690; 428/917

(58) Field of Classification Search .................. None
See application file for complete search history.

(56) References Cited

U.S. PATENT DOCUMENTS

| | | | |
|---|---|---|---|
| 6,713,192 B2 | 3/2004 | Fukuoka et al. | 428/690 |
| 7,129,386 B2 | 10/2006 | Saitoh et al. | 585/26 |
| 7,173,131 B2 | 2/2007 | Saitoh et al. | 544/336 |
| 7,241,513 B2 | 7/2007 | Suzuki et al. | 428/690 |
| 7,309,533 B2 | 12/2007 | Saitoh et al. | 428/690 |
| 2005/0236977 A1 | 10/2005 | Yamada et al. | 313/504 |
| 2006/0043858 A1 | 3/2006 | Ikeda et al. | 313/250 |
| 2006/0097227 A1 | 5/2006 | Okajima et al. | 252/301.16 |
| 2006/0121312 A1 | 6/2006 | Yamada et al. | 428/690 |
| 2006/0154105 A1 | 7/2006 | Yamamoto et al. | 428/690 |
| 2007/0111029 A1 | 5/2007 | Yamada et al. | 428/690 |
| 2007/0152565 A1* | 7/2007 | Kubota et al. | 313/504 |

FOREIGN PATENT DOCUMENTS

| | | |
|---|---|---|
| EP | 1696015 | 8/2006 |
| JP | 10-189248 | 7/1998 |
| JP | 2001-257074 | 9/2001 |
| JP | 2001-257075 | 9/2001 |
| JP | 2001-284050 | 10/2001 |
| JP | 2002/069044 | 3/2002 |
| JP | 2003/238534 | 8/2003 |

(Continued)

*Primary Examiner* — Angela Ortiz
*Assistant Examiner* — Brett A Crouse
(74) *Attorney, Agent, or Firm* — Fitzpatrick, Cella, Harper & Scinto

(57) ABSTRACT

To provide a novel fluoranthene derivative and an organic light emitting device having the fluoranthene derivative.

2 Claims, 2 Drawing Sheets

FOREIGN PATENT DOCUMENTS

| | | |
|---|---|---|
| JP | 2004/002297 | 1/2004 |
| JP | 2006/100756 | 4/2006 |
| WO | 2004/018587 | 3/2004 |
| WO | 2005/061656 | 7/2005 |
| WO | 2007/021117 | 2/2007 |
| WO | WO 2007/072741 | * 6/2007 |
| WO | WO 2007/072742 | * 6/2007 |
| WO | WO 2007/072952 | * 6/2007 |
| WO | WO 2007/123259 | * 11/2007 |
| WO | WO 2007/125809 | * 11/2007 |

* cited by examiner

COMPOUND AND ORGANIC LIGHT EMITTING DEVICE

TECHNICAL FIELD

The present invention relates to a compound and a light emitting device using the compound.

DESCRIPTION OF THE RELATED ART

Recent progress in an organic light emitting device is remarkable. The organic light emitting device has such characteristics that it can be turned into a thin, lightweight light emitting device which: provides high luminance at a low applied voltage; and has the diversity of a luminous wavelength and high-speed responsiveness. The characteristics suggest that the light emitting device may be used in a wide variety of applications.

However, the organic light emitting device still involves a large number of problems in terms of durability such as a change over time due to long-term use and deterioration due to: an atmospheric gas containing oxygen or moisture. When the application of the device to a full-color display is taken into consideration, the emission of blue, green, or red light with an additionally long lifetime, additionally high conversion efficiency, and an additionally high color purity has been needed at present, and various proposals have been made to cope with the application.

In addition, examples of a patent document concerning an organic light emitting device include Japanese Patent Application Laid-Open No. H10-189248, International Publication No. WO 2005/061656, Japanese Patent Application Laid-Open No. 2002-69044, and Japanese Patent Application Laid-Open No. 2001-284050.

The present invention has been made with a view to solving such problems of the prior art, and an object of the present invention is to provide a compound for an organic light emitting device showing a light emission hue with an extremely good purity and having an optical output with high efficiency, high luminance, and a long lifetime. Another object of the present invention is to provide an organic light emitting device that can be easily produced at a relatively low cost.

DISCLOSURE OF THE INVENTION

The inventors of the present invention have made extensive studies with a view to solving the above-mentioned problems. As a result, they have completed the present invention.

That is, according to the present invention, there is provided a compound represented by the following general formula (1):

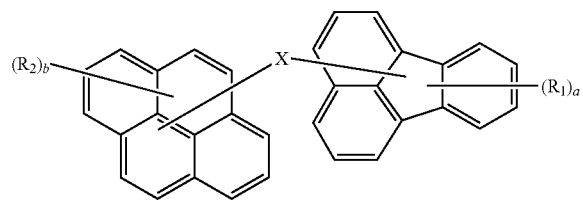

(1)

where $R_1$ and $R_2$ each represent a group selected from the group consisting of a hydrogen atom, a halogen atom, a substituted or unsubstituted alkyl group, a substituted or unsubstituted aralkyl group, a substituted or unsubstituted alkoxy group, a substituted or unsubstituted aryl group, and a substituted or unsubstituted heterocyclic group, $R_1$'s or $R_2$'s may be identical to or different from each other, and $R_1$ and $R_2$ may be identical to or different from each other, X represents a divalent arylene group which is a divalent aromatic group selected from a substituted or unsubstituted naphthylene group, a substituted or unsubstituted phenanthrylene group, a substituted or unsubstituted anthrylene group, a substituted or unsubstituted chrysenylene group, a substituted or unsubstituted dibenzo[a,h]anthrylene group, a substituted or unsubstituted naphthacenylene group, a substituted or unsubstituted pentacenylene group, and a substituted or unsubstituted perylenylene group, $R_1$'s or $R_2$'s may be bonded to each other to form a ring, and a and b each represent an integer of 1 to 9.

The compound of the present invention has a high glass transition temperature, and the incorporation of the compound of the present invention particularly as a host or guest for a light emitting layer can provide highly efficient light emission. An organic light emitting device of the present invention emits light with high efficiency at a low applied voltage, has high heat stability, and is excellent in durability.

DESCRIPTION OF THE EMBODIMENTS

Figure 1:
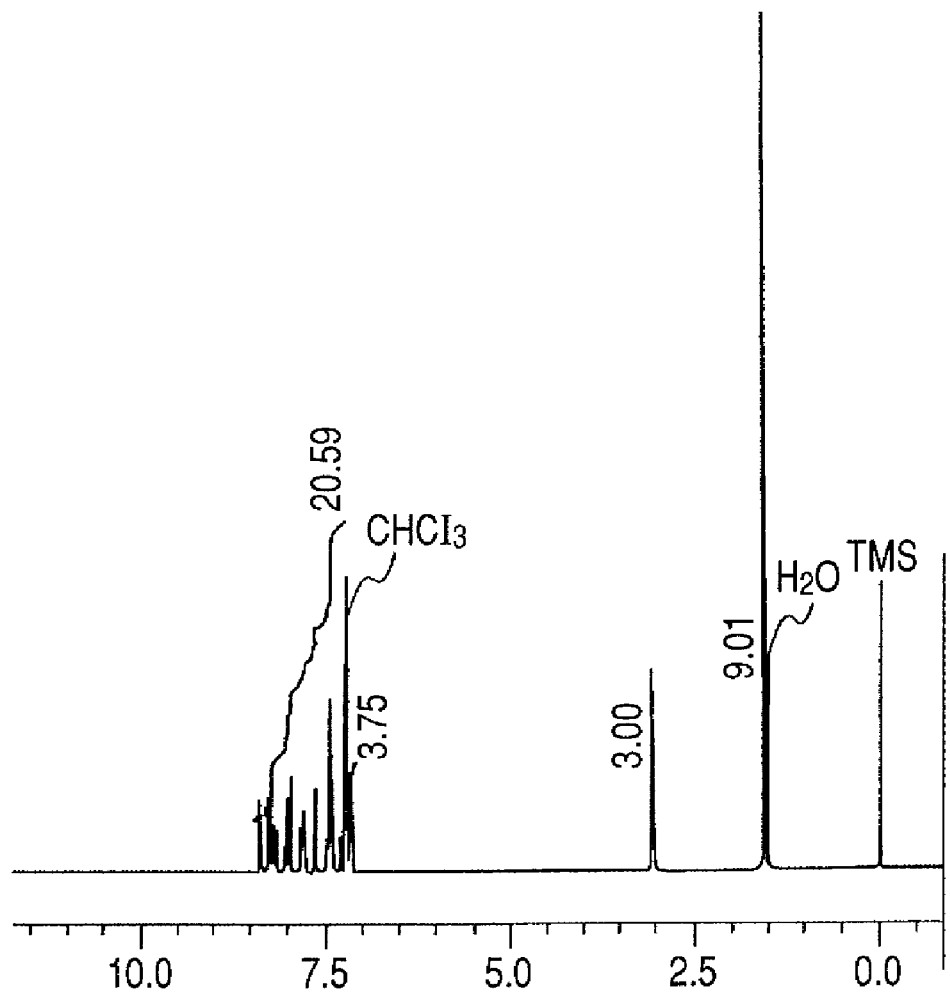
FIG. 1 is a view showing the $^1$H-NMR (CDCl$_3$) spectrum of Exemplified Compound No. 101 in the present invention.

Provided is a compound represented by the following general formula (1):

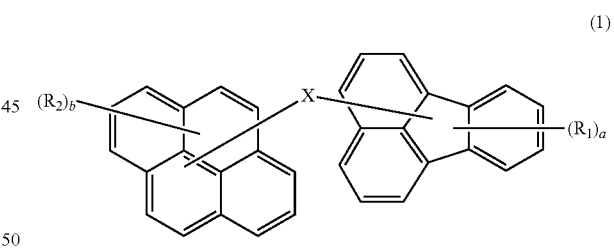

(1)

where $R_1$ and $R_2$ each represent a group selected from the group consisting of a hydrogen atom, a halogen atom, a substituted or unsubstituted alkyl group, a substituted or unsubstituted aralkyl group, a substituted or unsubstituted alkoxy group, a substituted or unsubstituted aryl group, and a substituted or unsubstituted heterocyclic group, $R_1$'s or $R_2$'s may be identical to or different from each other, and $R_1$ and $R_2$ may be identical to or different from each other, X represents a divalent arylene group which is a divalent aromatic group selected from a substituted or unsubstituted naphthylene group, a substituted or unsubstituted phenanthrylene group, a substituted or unsubstituted anthrylene group, a substituted or unsubstituted chrysenylene group, a substituted or unsubstituted dibenzo[a,h]anthrylene group, a substituted or unsubstituted naphthacenylene group, a substituted or unsubstituted pentacenylene group, and a substituted or unsubstituted perylenylene group, R₁'s or R₂'s may be bonded to each other to form a ring, and a and b each represent an integer of 1 to 9.

Further, provided is a compound in which X in the general formula (1) represents a substituted or unsubstituted anthrylene group so that the compound is represented by the following general formula (2):

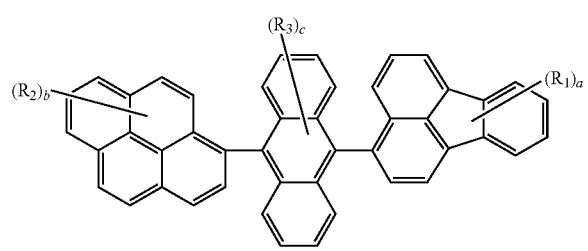

(2)

where R₁ to R₃ each represent a group selected from the group consisting of a hydrogen atom, a halogen atom, a substituted or unsubstituted alkyl group, a substituted or unsubstituted aralkyl group, a substituted or unsubstituted alkoxy group, a substituted or unsubstituted aryl group, and a substituted or unsubstituted heterocyclic group, R₁'s, R₂'s, or R₃'s may be identical to or different from each other, and R₁, R₂, and R₃ may be identical to or different from each other, R₁'s, R₂'s, or R₃'s may be bonded to each other to form a ring, a and b each represent an integer of 1 to 9, and c represents an integer of 1 to 8.

Further, provided is a compound represented by the following general formula (3):

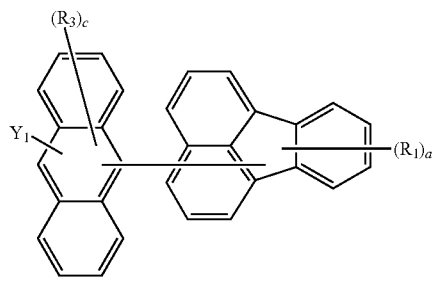

[3]

where R₁ and R₃ each represent a group selected from the group consisting of a hydrogen atom, a halogen atom, a substituted or unsubstituted alkyl group, a substituted or unsubstituted aralkyl group, a substituted or unsubstituted alkoxy group, a substituted or unsubstituted aryl group, and a substituted or unsubstituted heterocyclic group, R₁'s or R₃'s may be identical to or different from each other, and R₁ and R₃ may be identical to or different from each other, Y₁ represents a fused ring aromatic group selected from a substituted or unsubstituted naphthyl group, a substituted or unsubstituted phenanthryl group, a substituted or unsubstituted acenaphthyl group, a substituted or unsubstituted acephenanthryl group, a substituted or unsubstituted aceanthryl group, a substituted or unsubstituted benzo[a]anthryl group, a substituted or unsubstituted triphenylenyl group, a substituted or unsubstituted chrysenyl group, a substituted or unsubstituted benzo[c]phenanthryl group, a substituted or unsubstituted naphthacenyl group, a substituted or unsubstituted pentacenyl group, a substituted or unsubstituted dibenzo[a,h]anthryl group, a substituted or unsubstituted picenyl group, and a substituted or unsubstituted perylenyl group, R₁'s or R₃'s may be bonded to each other to form a ring, a represents an integer of 1 to 9, and c represents an integer of 1 to 8.

In addition, according to the present invention, there is provided an organic light emitting device including one or more layers each containing an organic compound, the one or more layers being interposed between a pair of electrodes formed of an anode and a cathode at least one of which is transparent or semitransparent, in which at least one layer of the one or more layers each containing an organic compound contains at least one kind of a fluoranthene compound represented by any one of the general formulae (1) to (3) and having, as a substituent, a fused ring aromatic group which is bicyclic or more and which substitutes for a fused ring aromatic group or heterocyclic group which is bicyclic or more.

Further, according to the present invention, there is provided an organic light emitting device in which the layer containing at least one kind of a compound represented by any one of the general formulae (1) to (3) is at least one layer having a light emitting region.

Further, according to the present invention, there is provided an organic light emitting device in which the at least one layer having the light emitting region is a light emitting layer.

Further, according to the present invention, there is provided an organic light emitting device in which the light emitting layer is formed of at least two kinds of compounds including a host and a guest.

Hereinafter, the present invention will be described in detail.

First, a fluoranthene compound of the present invention characterized by being substituted by a specific fused ring aromatic group which is bicyclic or more and which has a selected fused ring aromatic group or heterocyclic group which is bicyclic or more will be described.

A compound to be used in the present invention can be used as a material for an organic light emitting device. When the compound is used for a light emitting layer in the device, the compound can be used in the light emitting layer alone and to serve as a dopant (guest) material or a host material. Thus, a device emitting light with high efficiency, maintaining high luminance for a long time period, and showing small deterioration due to energization can be obtained.

When a light emitting layer is formed of a carrier transportable host material and a guest, a main process for light emission includes the following several steps:

1. the transport of electrons or holes in the light emitting layer;
2. the generation of excitons of the host material;
3. the transfer of excitation energy between host material molecules; and
4. the movement of the excitation energy from the host material to the guest.

Desired energy movement in each step and light emission occur in competition with various deactivation steps.

Needless to say, the light emission quantum efficiency of a light emission central material itself must be large in order to improve the luminous efficiency of an EL (electroluminescence) device. However, the efficiency with which energy movement between host molecules or between host and guest molecules can be performed is also of great concern. In addition, the deterioration of light emission due to energization is assumed to be related to a change in environment surrounding a light emitting material due to at least the light emission central material itself or a molecule around the light emission central material, though no causes for the deterioration have been revealed at present.

In view of the foregoing, the inventors of the present invention have made various studies.

First, a compound represented by the following general formula (4) in which different fused ring aromatic groups were bonded, and, furthermore, a fluoranthenyl group was introduced so that an electron trap effect might be expected was investigated:

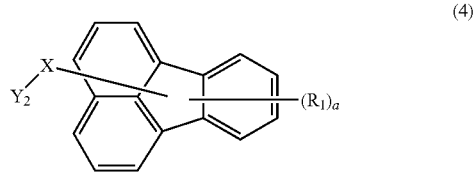

(4)

In the general formula (4), $R_1$ represents group selected from the group consisting of a hydrogen atom, a halogen atom, a substituted or unsubstituted alkyl group, a substituted or unsubstituted aralkyl group, a substituted or unsubstituted alkoxy group, a substituted or unsubstituted aryl group, and a substituted or unsubstituted heterocyclic group, and may be identical to or different from each other. X represents a divalent arylene group and a divalent aromatic group selected from the group consisting of a substituted or unsubstituted naphthylene group, a substituted or unsubstituted phenanthrylene group, a substituted or unsubstituted anthrylene group, a substituted or unsubstituted chrysenylene group, a substituted or unsubstituted dibenzo[a,c]anthrylene group, a substituted or unsubstituted benzo[a,h]anthrylene group, a substituted or unsubstituted naphthacenylene group, a substituted or unsubstituted pentacenylene group, and a substituted or unsubstituted perylenylene group. $Y_2$ represents a fused ring aromatic group selected from the group consisting of a substituted or unsubstituted naphthyl group, a substituted or unsubstituted phenanthryl group, a substituted or unsubstituted acenaphthyl group, a substituted or unsubstituted acephenanthryl group, a substituted or unsubstituted aceantolyl group, a substituted or unsubstituted benzo[a]anthryl group, a substituted or unsubstituted pyrenyl group, a substituted or unsubstituted triphenylenyl group, a substituted or unsubstituted chrysenyl group, a substituted or unsubstituted benzo[c]phenanthryl group, a substituted or unsubstituted naphthacenyl group, a substituted or unsubstituted pentacenyl group, a substituted or unsubstituted dibenzo[a,c]antolyl group, a substituted or unsubstituted dibenzo[a,h]antolyl group, a substituted or unsubstituted picenyl group, and a substituted or unsubstituted perylenyl group, or a substituted or unsubstituted heterocyclic group. $R_1$'s may bind with each other to form a ring. a represents an integer of 1 to 9.

As a result, the inventors have paid attention to a fluoranthene compound characterized by having, as a substituent, a fused ring aromatic group which is bicyclic or more and which substitutes for a fused ring aromatic group or heterocyclic group which is bicyclic or more. Then, the inventors have invented a compound represented by any one of the general formulae (1) to (3) and an organic light emitting device using the compound. The inventors have found that, in particular, a device using the compound as a host or guest for its light emitting layer among the organic light emitting devices emits light with high efficiency, maintains high luminance for a long time period, and shows small deterioration due to energization.

One possible cause for the deterioration of the light emission due to the energization is the deterioration of the thin-film shape of the light emitting layer. The deterioration of the thin-film shape may result from the crystallization of the organic thin film due to, for example, the temperature of an environment in which the device is driven or heat generation at the time of the driving of the device. The crystallization may originate from the low glass transition temperature of a material for the thin film, so it is desired that an organic EL material have a high glass transition temperature. An improvement in durability of an organic EL device can be expected from the compound of the present invention because the compound has a high glass transition temperature (for example, 216° C. for Exemplified Compound No. 101).

The compound to be used in the present invention is a fluoranthene compound characterized by having, as a substituent, a fused ring aromatic group which is bicyclic or more and which substitutes for a fused ring aromatic group or heterocyclic group which is bicyclic or more. Therefore, the molecular structure of the fluoranthene compound which can be formed is such that rotation between respective fused ring aromatic groups in any one of the molecules of the compound is restrained. In the present invention, a molecule of the compound was designed while the suppression of molecular vibration due to the structural factor and the wave form of emitted light with no vibrational structure in association with the vibration were taken into consideration. In addition, from the viewpoint of quantum efficiency, substituents each having a fused ring aromatic structure such as anthracene, pyrene, or fluoranthene are preferably combined for realizing high quantum efficiency. Further, in order that concentration quenching due to an interaction between the fused ring aromatic groups of the molecules of the compound may be suppressed, the introduction of a steric hindrance group such as a tert-butyl group in a fused ring aromatic group is also preferable for an improvement in quantum efficiency.

In addition, as described above, a compound to be used in an organic light emitting device is required to have a high glass transition temperature. In general, a material having a large molecular weight has a high glass transition temperature. The fluoranthene compound of the present invention is a fluoranthene compound characterized by having, as a substituent, a fused ring aromatic group which is bicyclic or more and which substitutes for a fused ring aromatic group or heterocyclic group which is bicyclic or more. Moreover, the fluoranthene compound has a molecular weight of about 500 or more to 900 or less; the molecular weight is proper when the property with which the compound is deposited from the vapor is taken into consideration. Fluoranthene having, as a substituent, only a small aromatic ring such as a phenyl group or a tolyl group has a molecular weight smaller than that of the fluoranthene compound of the present invention, so a high glass transition temperature may not be expected from such fluoranthene. In addition, the introduction of only an alkyl group may reduce the glass transition temperature of a compound to be obtained. The present invention has been made by designing a molecule of the fluoranthene compound on the basis of the foregoing discussion.

Note that when the fluoranthene compound of the present invention is used as a dopant material, the following numeric value range is a preferred numeric value range. That is, a dopant concentration with respect to the host material is 0.01 wt % or more to 80 wt % or less, or preferably 1 wt % or more to 40 wt % or less. The dopant material may be incorporated into the entirety of a layer formed of the host material uniformly or with a concentration gradient. Alternatively, the dopant material may be incorporated into a certain region of the host material layer partially so that a region of the host material layer containing no dopant material is present.

In the compound of the present invention, a hydrogen substituent may be substituted by deuterium.

In the compound of the present invention, examples of a substituted or unsubstituted alkyl group include, but are not limited to: a methyl group; a methyl-dl group; a methyl-d3 group; an ethyl group; an ethyl-d5 group; an n-propyl group; an n-butyl group; an n-pentyl group; an n-hexyl group; an n-heptyl group; an n-octyl group; an n-decyl group; an iso-propyl group; an iso-propyl-d7 group; an iso-butyl group; a sec-butyl group; a tert-butyl group; a tert-butyl-d9 group; an iso-pentyl group; a neopentyl group; a tert-octyl group; a fluoromethyl group; a difluoromethyl group; a trifluoromethyl group; a 2-fluoroethyl group; a 2,2,2-trifluoroethyl group; a perfluoroethyl group; a 3-fluoropropyl group; a perfluoropropyl group; a 4-fluorobutyl group; a perfluorobutyl group; a 5-fluoropentyl group; a 6-fluorohexyl group; a chloromethyl group; a trichloromethyl group; 2-chloroethyl group; a 2,2,2-trichloroethyl group; a 4-chlorobutyl group; a 5-chloropentyl group; a 6-chlorohexyl group; a bromomethyl group; a 2-bromoethyl group; an iodomethyl group; a 2-iodoethyl group; a hydroxymethyl group; a hydroxyethyl group; a cyclopropyl group; a cyclobutyl group; a cyclopentyl group; a cyclohexyl group; a cyclopentylmethyl group; a cyclohexylmethyl group; a cyclohexylethyl group; a 4-fluorocyclohexyl group; a norbornyl group; and an adamantyl group.

Examples of a substituted or unsubstituted aralkyl group include, but are not limited to: a benzyl group; a 2-phenylethyl group; a 2-phenylisopropyl group; a 1-naphthylmethyl group; a 2-naphthylmethyl group; a 2-(1-napthyl)ethyl group; a 2-(2-napthyl)ethyl group; a 9-anthrylmethyl group; a 2-(9-anthryl)ethyl group; a 2-fluorobenzyl group; a 3-fluorobenzyl group; a 4-fluorobenzyl group; a 2-chlorobenzyl group; a 3-chlorobenzyl group; a 4-chlorobenzyl group; a 2-bromobenzyl group; a 3-bromobenzyl group; and a 4-bromobenzyl group.

Examples of a substituted or unsubstituted aryl group include, but are not limited to: a phenyl group; a phenyl-d5 group; a 4-methylphenyl group; a 4-methoxyphenyl group; a 4-ethylphenyl group; a 4-fluorophenyl group; a 4-trifluorophenyl group; a 3,5-dimethylphenyl group; a 2,6-diethylphenyl group; a mesityl group; a 4-tert-butylphenyl group; a ditolylaminophenyl group; a biphenyl group; a terphenyl group; a naphthyl group; a naphthyl-d7 group; an acenaphthylenyl group; an anthryl group; an anthryl-d9 group; a phenanthryl group; a phenanthryl-d9 group; a pyrenyl group; a pyrenyl-d9 group; an acephenanthrylenyl group; an aceanthrylenyl group; a chrysenyl group; a dibenzo chrysenyl group; a benzoanthryl group; a benzoanthryl-d11 group; a dibenzo[a,h]anthryl group; a naphthacenyl group; a picenyl group; a pentacenyl group; a fluorenyl group; a triphenylenyl group; a perylenyl group; and a perylenyl-d11 group.

Examples of a substituted or unsubstituted heterocyclic group include, but are not limited to: a pyrrolyl group; a pyridyl group; a pyridyl-d5 group; a bipyridyl group; a methylpyridyl group; a pyrimidinyl group; a pyrazinyl group; a pyridazinyl group; a terpyrrolyl group; a thienyl group; a thienyl-d4 group; a terthienyl group; a propylthienyl group; a benzothienyl group; a dibenzothienyl group; a dibenzothienyl-d7 group; a furyl group; a furyl-d4 group; a benzofuryl group; an isobenzofuryl group; dibenzofuryl group; a dibenzofuryl-d7 group; a quinolyl group; a quinolyl-d6 group; an isoquinolyl group; a quinoxalinyl group; a naphthylidinyl group; a quinazolinyl group; a phenanthridinyl group; an indolizinyl group; a phenazinyl group; a carbazolyl group; an oxazolyl group; an oxadiazolyl group; a thiazolyl group; a thiadiazolyl group; an acridinyl group; and a phenazinyl group.

Examples of a substituted or unsubstituted alkoxy group include: an alkyloxy group or aralkyloxy group having the above-mentioned substituted or unsubstituted alkyl group or aralkyl group; and an aryloxy group having the above-mentioned substituted or unsubstituted aryl group or heterocyclic group. Specific examples thereof include, but are not limited to: a methoxy group; an ethoxy group; a propoxy group; a 2-ethyl-octyloxy group; a phenoxy group; a 4-tert-butylphenoxy group; a benzyloxy group; and a thienyloxy group.

Examples of a halogen atom include: fluorine; chlorine; bromine; and iodine.

The substituent may further have a substituent including: an alkyl group such as a methyl group, an ethyl group, or a propyl group; an aryl group such as a phenyl group or a biphenyl group; a heterocyclic group such as a thienyl group, a pyrrolyl group, or a pyridyl group; an amino group such as a dimethylamino group, a diethylamino group, a dibenzylamino group, a diphenylamino group, a ditolylamino group, or a dianisolyl group; an alkoxy group such as a methoxy group or an ethoxy group; a halogen atom such as fluorine, chlorine, bromine, or iodine; a hydroxyl group; a cyano group; a nitro group, but the substituent is not limited thereto.

Further, specific examples of the fluoranthene compound to be used in the present invention characterized by being substituted by a specific fused ring aromatic group which is bicyclic or more and which has a selected fused ring aromatic group or heterocyclic group which is bicyclic or more are listed in Table 1 below. However, the present invention is of course not limited to these examples. In Table 1, the compound to be used in the present invention is represented by A-B-C, and the position to which A or C is bonded is shown in B. That is, Exemplified Compound No. 101 is represented as shown below.

TABLE 1
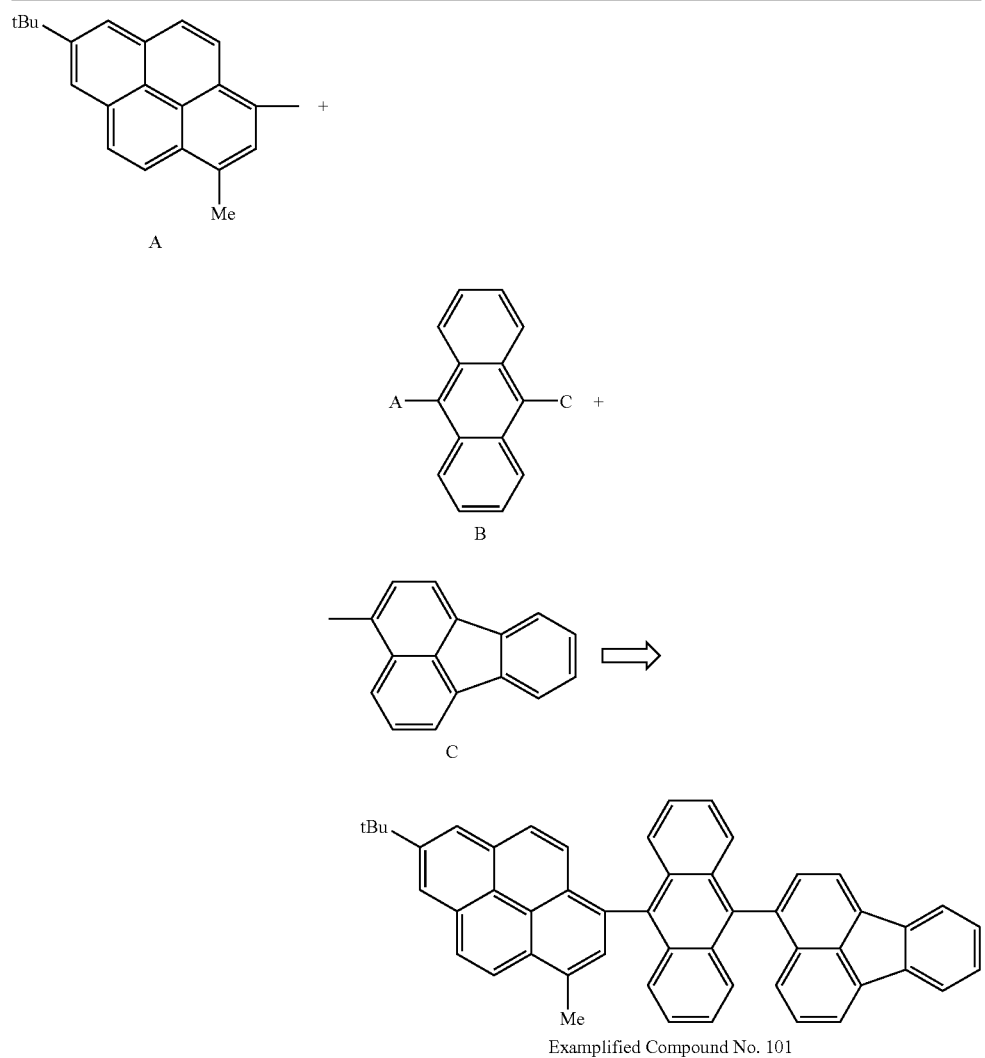

TABLE 1-continued

| 103 | (pyrene with iPr and Me substituents) | anthracene with A and C | fluoranthene |
| 104 | (pyrene with tBu substituent) | anthracene with A and C | fluoranthene |
| 105 | (pyrene with two tBu substituents) | anthracene with A and C | fluoranthene |
| 106 | (pyrene) | anthracene with A and C | fluoranthene |
| 107 | (pyrene) | anthracene with A and C | fluoranthene |
| 108 | (pyrene with tBu and Me substituents) | anthracene with two Me groups, A and C | fluoranthene |

TABLE 1-continued
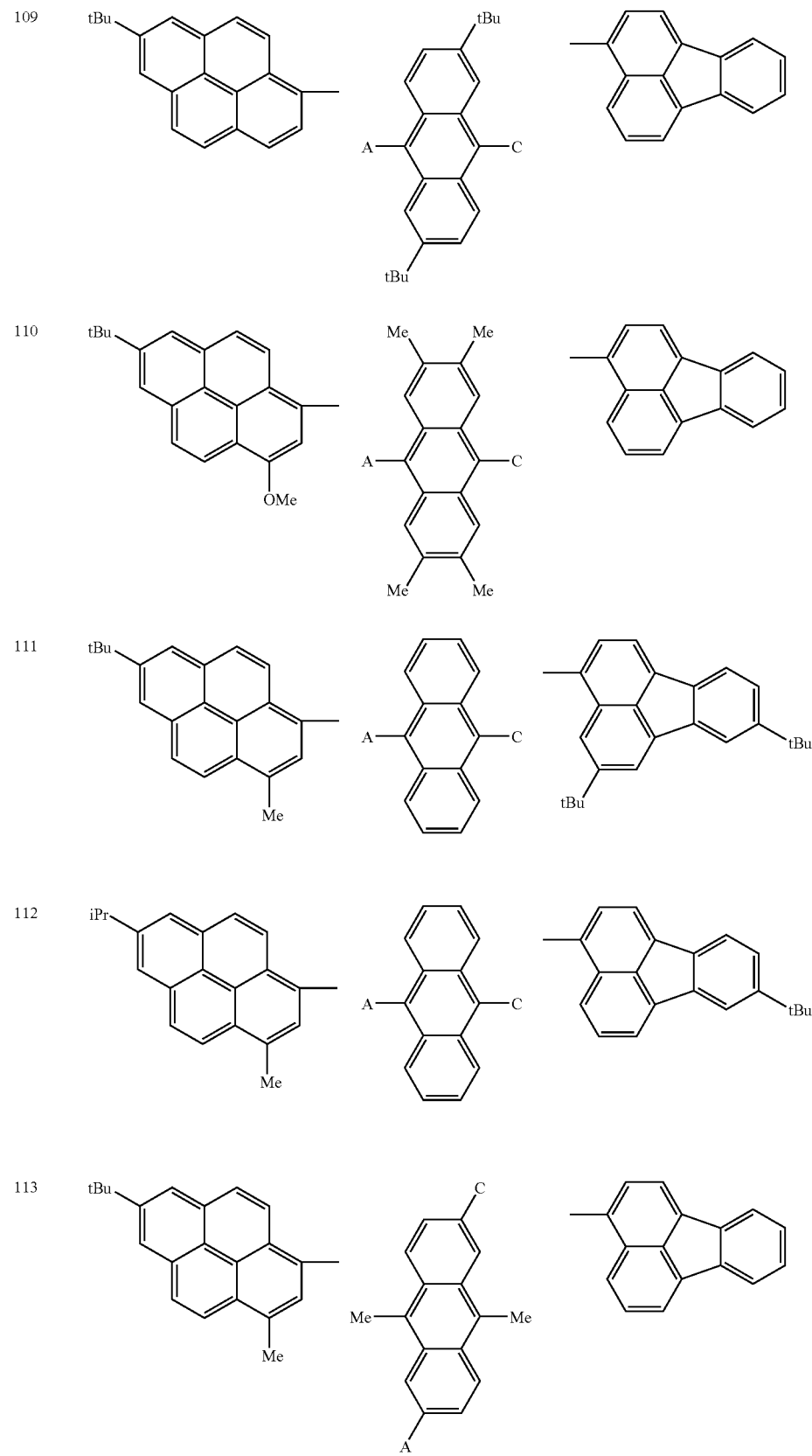

TABLE 1-continued
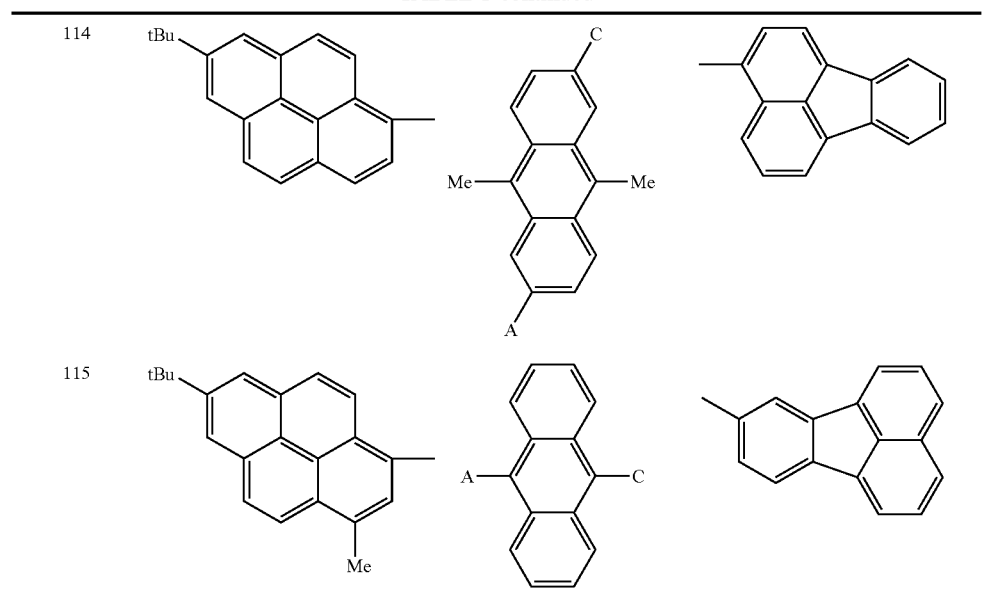
TABLE 2
A—B—C
| Compound No. | A | B | C |
| --- | --- | --- | --- |
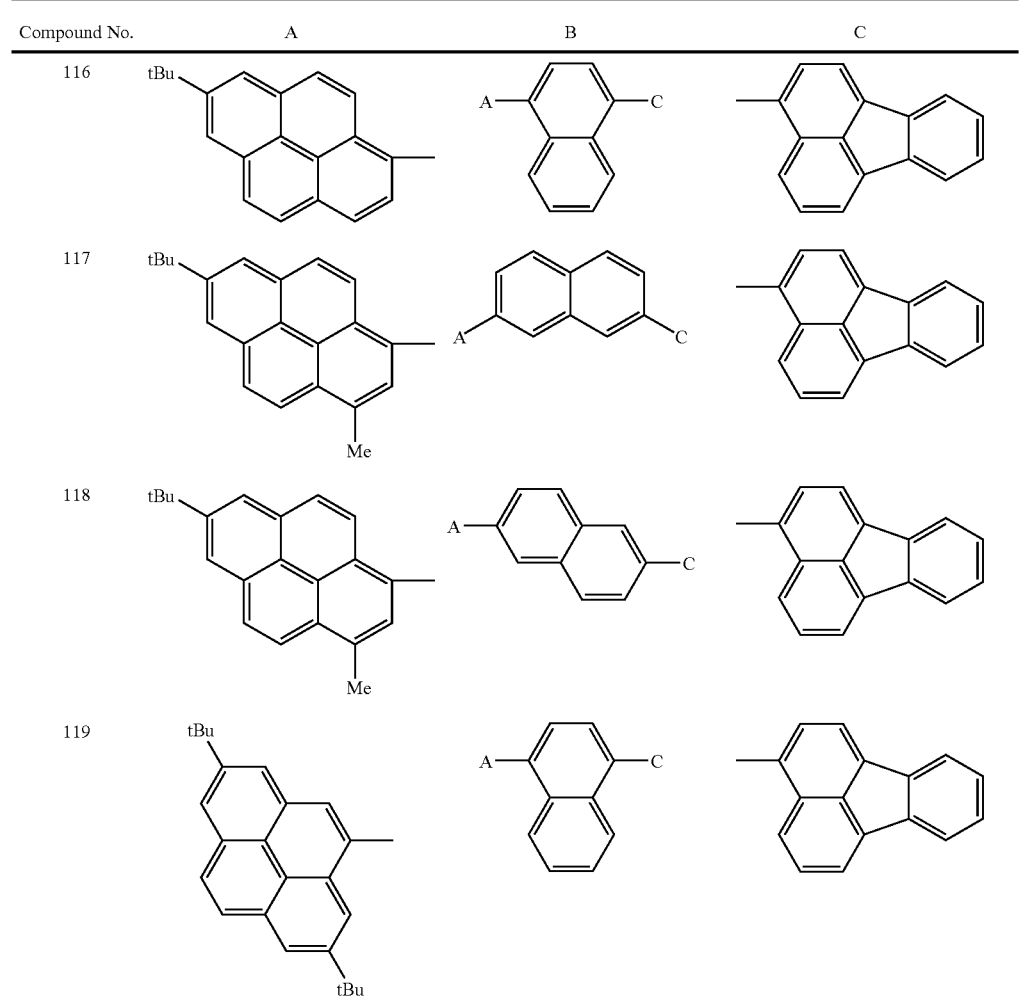

TABLE 2-continued

| Compound No. | A | B | C |
|---|---|---|---|
| 120 | pyrenyl | 2,6-naphthylene | tBu-fluoranthenyl |
| 121 | tBu-pyrenyl | 1,5-naphthylene | fluoranthenyl |
| 122 | tBu,tBu-pyrenyl | 1,5-naphthylene | fluoranthenyl |
| 123 | tBu,Me-pyrenyl | 1,5-naphthylene | fluoranthenyl |
| 124 | tBu-pyrenyl | 2,6-Me₂-1,5-naphthylene | fluoranthenyl |
| 125 | tBu,Me-pyrenyl | 2,6-Me₂-1,5-naphthylene | tBu-fluoranthenyl |

TABLE 2-continued
| Compound No. | A | B | C |
|---|---|---|---|
| 126 | 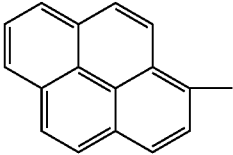 | 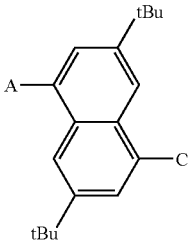 | 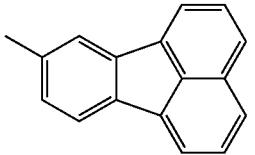 |
| 127 | 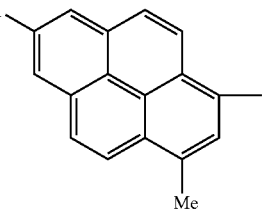 | 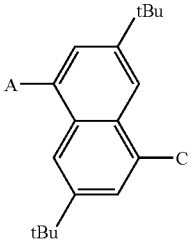 | 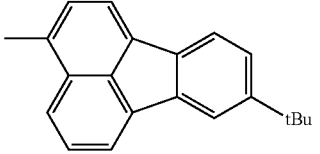 |
TABLE 3
| Compound No. | A | B | C |
|---|---|---|---|
| 128 | 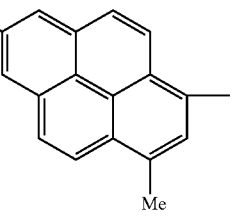 | 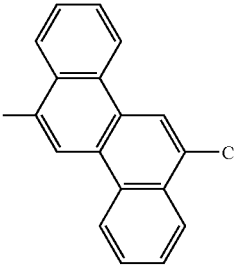 | 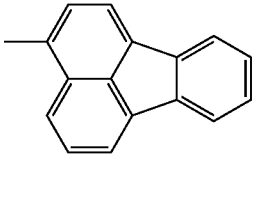 |
| 129 | 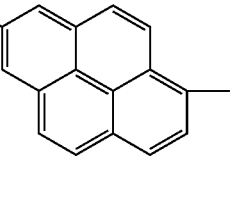 | 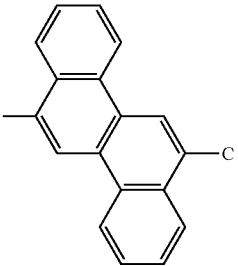 | 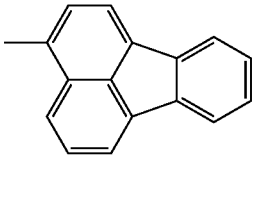 |
| 130 | 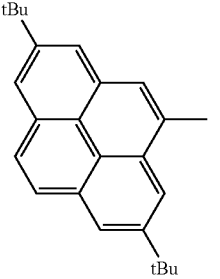 | 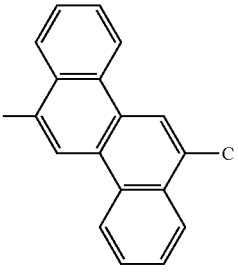 | 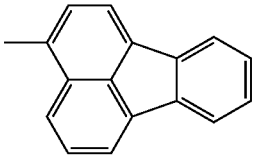 |

TABLE 3-continued

| Compound No. | A | B | C |
|---|---|---|---|
| 131 | tBu-pyrene | chrysene (A, C substituted) | methyl-fluoranthene-tBu |
| 132 | tBu-pyrene-Me | chrysene (A, C substituted) | methyl-fluoranthene |

TABLE 4

| Compound No. | A | B | C |
|---|---|---|---|
| 133 | tBu-pyrene-Me | phenanthrene (A, C substituted) | methyl-fluoranthene |
| 134 | tBu-pyrene-Me | phenanthrene (A, C substituted) | methyl-fluoranthene |
| 135 | tBu-pyrene | chrysene (A, C substituted) | methyl-fluoranthene |

TABLE 4-continued
| Compound No. | A | B | C |
|---|---|---|---|
| 136 | 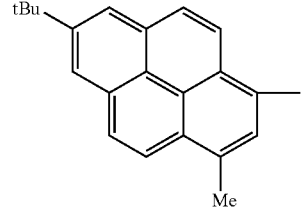 | 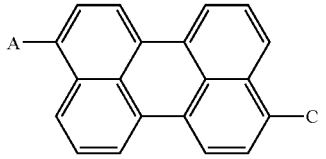 | 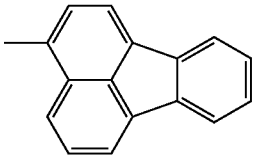 |
| 137 | 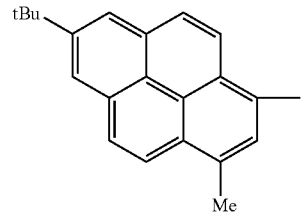 | 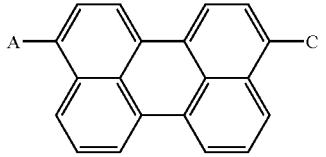 | 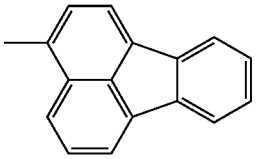 |
TABLE 5
| Compound No. | A | B | C |
|---|---|---|---|
| 138 | 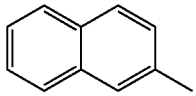 | 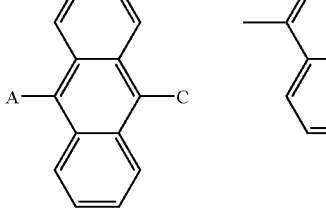 | 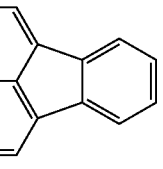 |
| 139 | 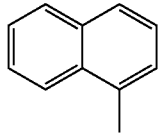 | 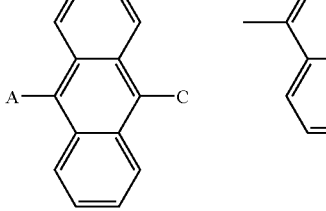 | 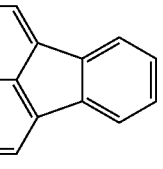 |
| 140 | 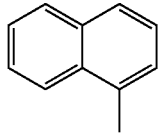 | 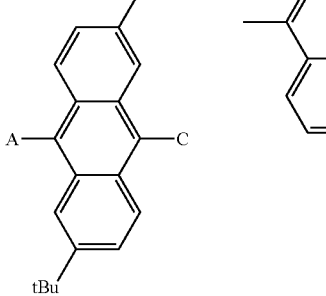 | 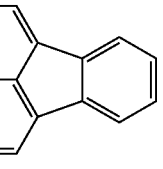 |

TABLE 5-continued
| Compound No. | A | B | C |
|---|---|---|---|
| 141 | 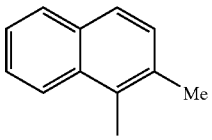 | 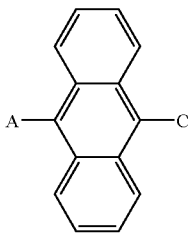 | 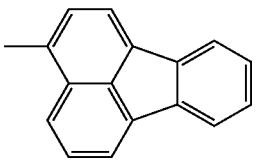 |
| 142 | 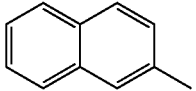 | 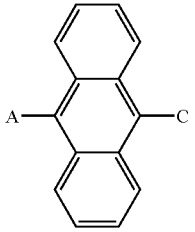 | 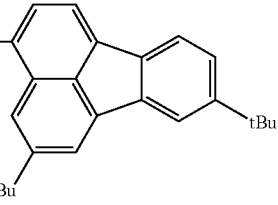 |
| 143 | 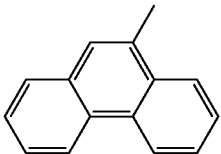 | 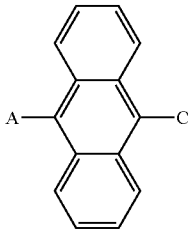 | 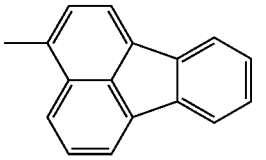 |
| 144 | 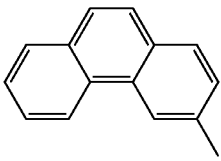 | 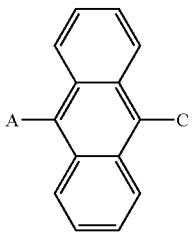 | 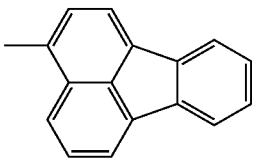 |
| 145 | 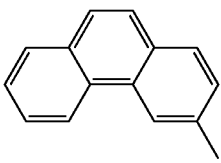 | 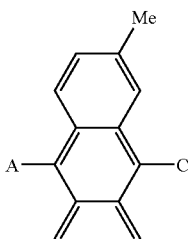 | 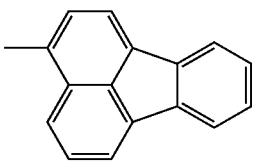 |
| 146 | 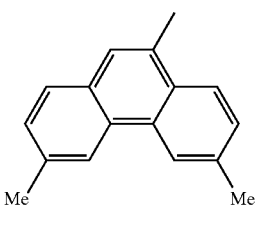 | 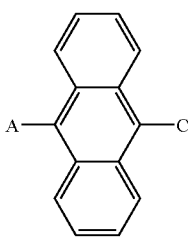 | 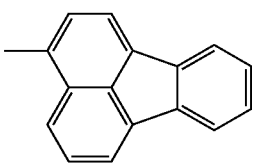 |

TABLE 5-continued
| Compound No. | A | B | C |
|---|---|---|---|
| 147 | 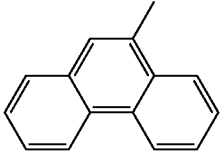 | 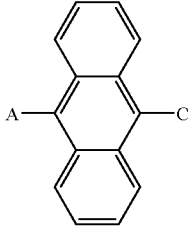 | 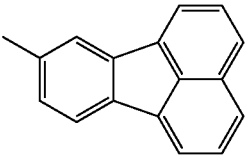 |
| 148 | 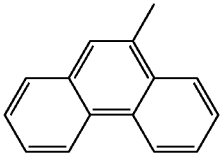 | 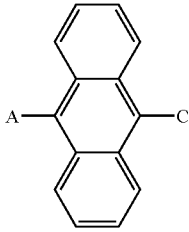 | 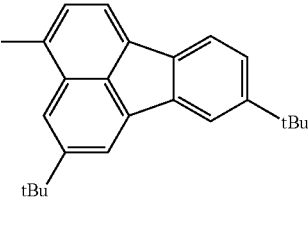 |
| 149 | 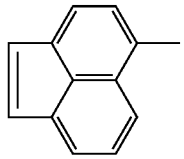 | 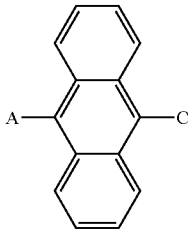 | 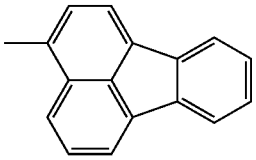 |
| 150 | 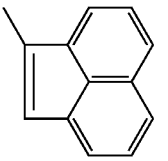 | 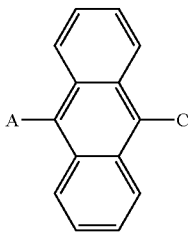 | 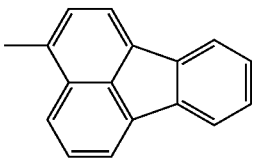 |
| 151 | 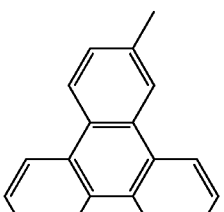 | 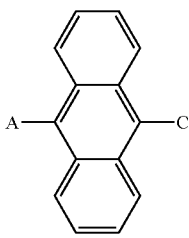 | 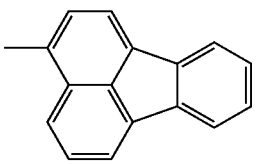 |
| 152 | 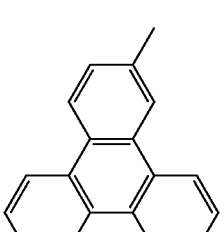 | 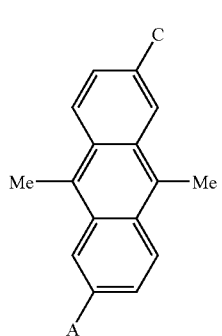 | 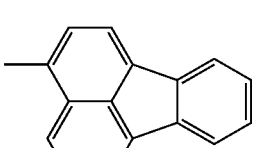 |

TABLE 5-continued
| Compound No. | A | B | C |
|---|---|---|---|
| 153 | 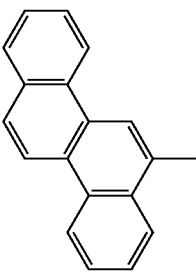 | 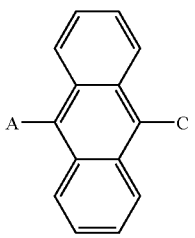 | 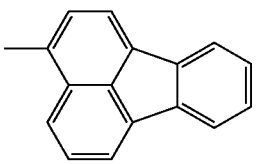 |
| 154 | 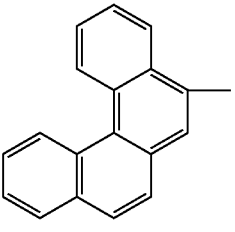 | 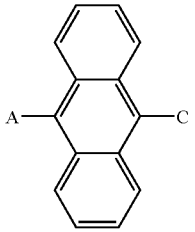 | 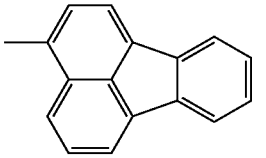 |
| 155 | 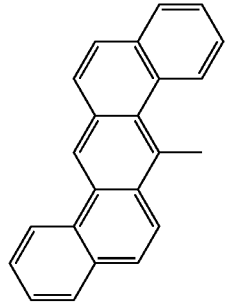 | 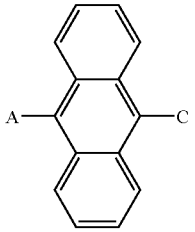 | 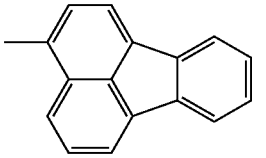 |
Examples of a compound represented by the general formula (4) except a compound represented by any one of the general formulae (1) to (3) are shown below as reference compounds.
TABLE 7
| Compound No. | A | B | C |
|---|---|---|---|
| 156 | 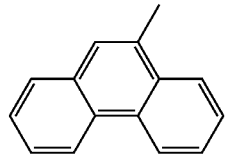 | 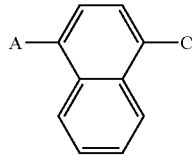 | 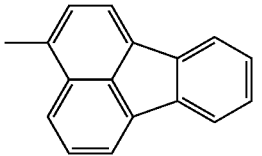 |
| 157 | 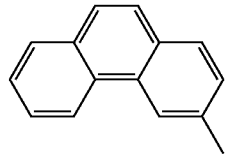 | 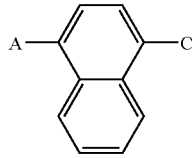 | 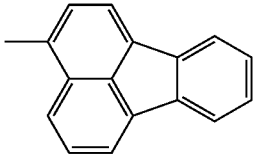 |

TABLE 7-continued
| Compound No. | A | B | C |
|---|---|---|---|
| 158 | 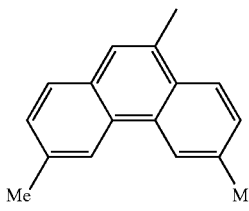 | 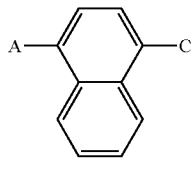 | 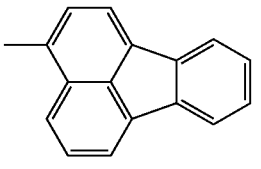 |
| 159 | 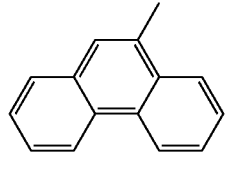 | 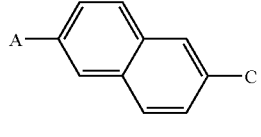 | 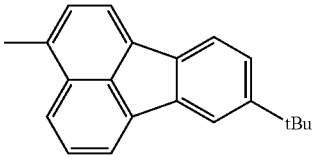 |
| 160 | 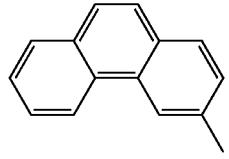 | 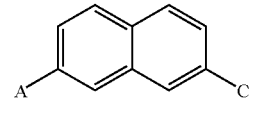 | 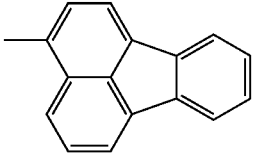 |
| 161 | 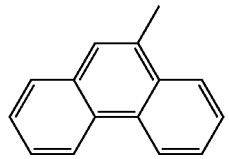 | 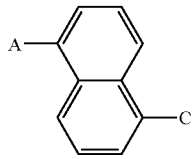 | 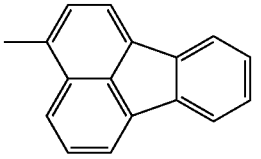 |
| 162 | 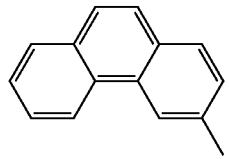 | 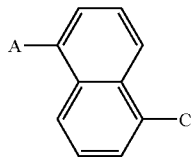 | 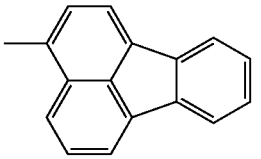 |
| 163 | 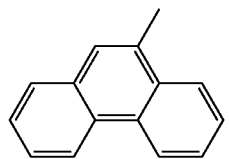 | 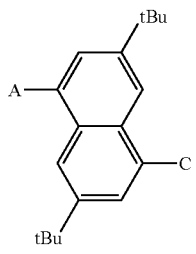 | 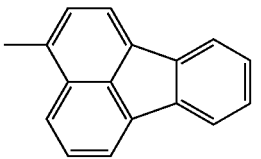 |
| 164 | 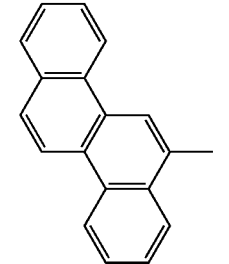 | 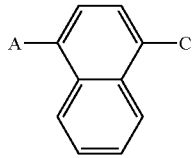 | 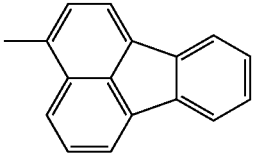 |

TABLE 7-continued
| Compound No. | A | B | C |
| --- | --- | --- | --- |
| 165 | 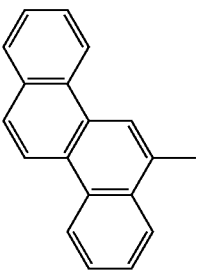 | 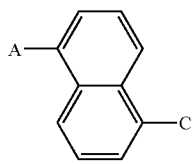 | 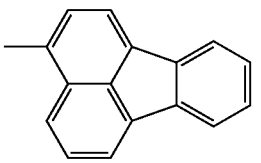 |
| 166 | 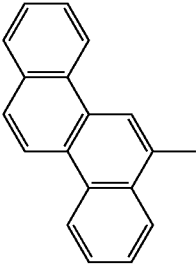 | 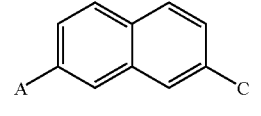 | 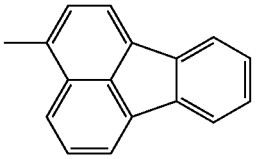 |
| 167 | 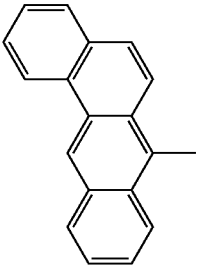 | 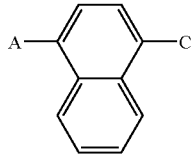 | 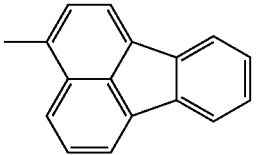 |
TABLE 8
| Compound No. | A | B | C |
| --- | --- | --- | --- |
| 168 | 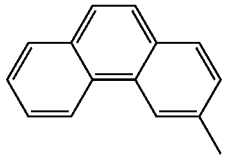 | 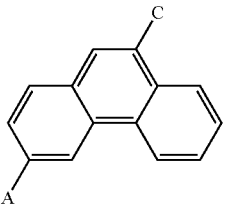 | 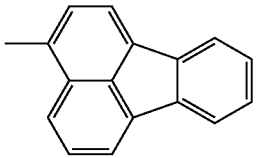 |
| 169 | 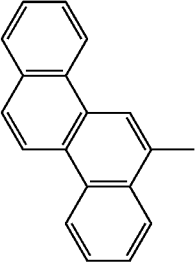 | 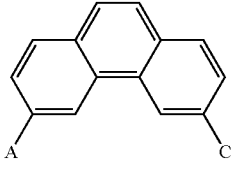 | 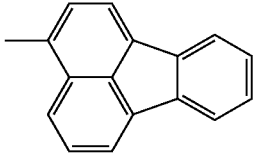 |

TABLE 8-continued
| Compound No. | A | B | C |
|---|---|---|---|
| 170 | 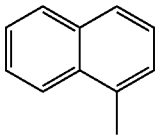 | 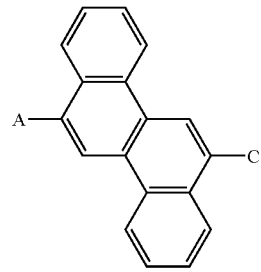 | 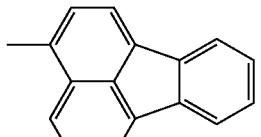 |
| 171 | 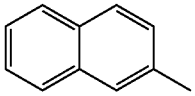 | 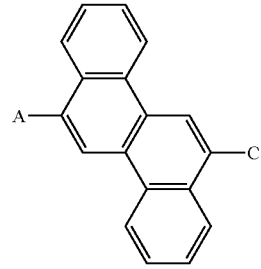 | 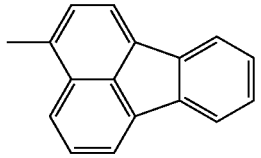 |
| 172 | 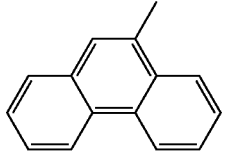 | 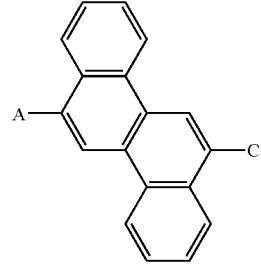 | 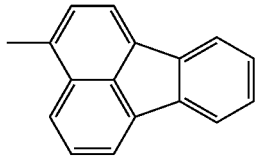 |
| 173 | 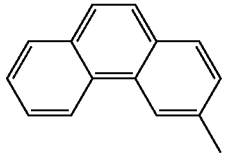 | 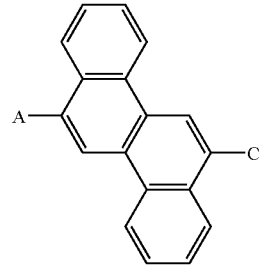 | 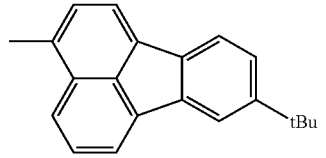 |
| 174 | 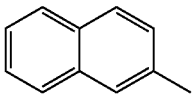 | 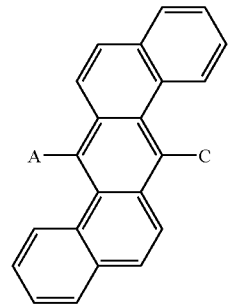 | 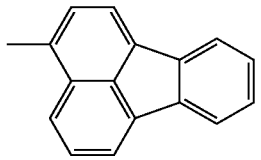 |

TABLE 8-continued
A—B—C
| Compound No. | A | B | C |
|---|---|---|---|
| 175 | 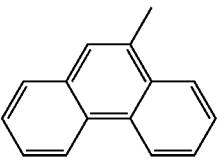 | 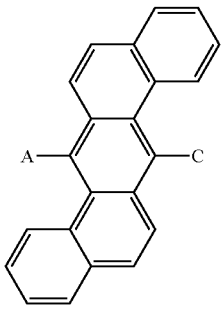 | 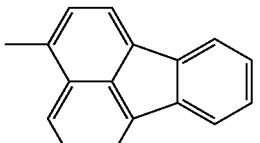 |
| 176 | 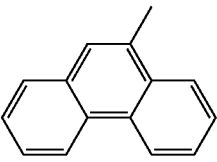 | 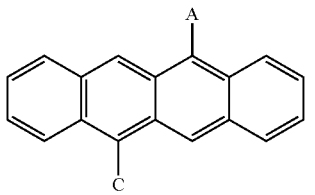 | 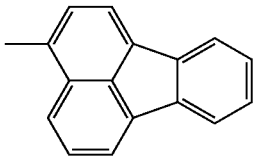 |
| 177 | 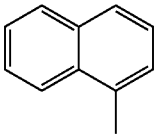 | 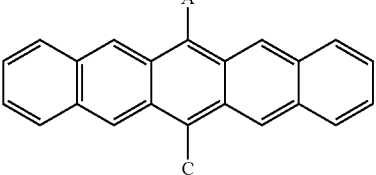 | 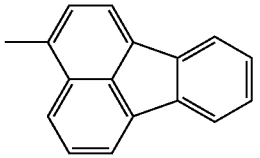 |
| 178 | 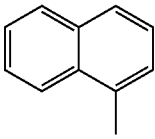 | 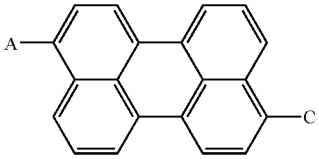 | 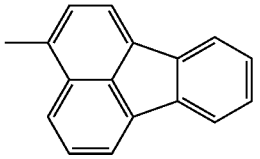 |
| 179 | 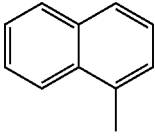 | 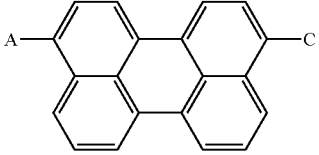 | 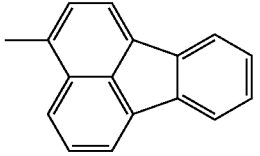 |
| 180 | 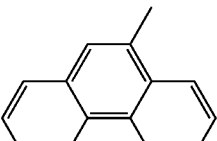 | 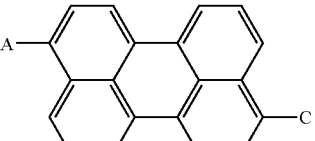 | 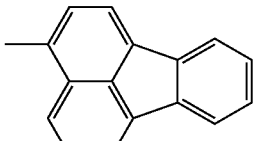 |
| 181 | 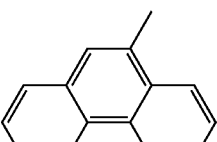 | 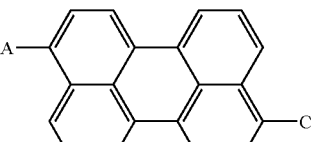 | 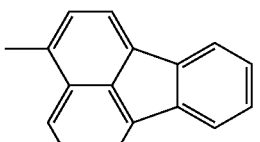 |

TABLE 9

A—B—C

| Compound No. | A | B | C |
| --- | --- | --- | --- |
| 9-1 | pyridinyl | naphthalene (A,C substituted) | fluoranthene |
| 9-2 | quinolinyl | naphthalene (A,C substituted) | fluoranthene |
| 9-3 | quinolinyl | chrysene (A,C substituted) | fluoranthene |
| 9-4 | quinolinyl | dibenz[a,h]anthracene (A,C substituted) | fluoranthene |

A method of synthesizing the compound of the present invention will be described below.

Of the compounds shown in Table 1, a compound substituted by a pyrenyl group having two substituents is preferably synthesized by: introducing a pyrenyl group in 9-bromoanthracene; brominating the resultant; and subjecting the resultant to Suzuki coupling with a fluoranthene boron body from the viewpoint of a synthesis yield. Alternatively, the pyrenyl group may be introduced by: causing the boron body of an A or C unit to react with 9,10-dibromoanthracene as a starting material; and causing the boron body of the remaining one of the A and C units to react with the remaining bromine portion. Of course, the synthesis method is not limited to the foregoing.

The compounds shown in Tables 2 to 4 each use the dibromo body of a B unit as a starting material. Each of the compounds can be synthesized by: causing the boron body of the A or C unit to react with the starting material by Suzuki coupling; and causing the boron body of the remaining one of the A and C units to react with the remaining bromine portion. Of course, the synthesis method is not limited to the foregoing.

A group of compounds shown in Tables 1, 2, 3, 5, and 6 is preferable from the viewpoints of the ease of availability of the central unit B and the simplicity of the synthesis of the dihalogen body or monohalogen body of the unit B. A chrysene unit exemplified in any one of Table 3 and other tables is also preferable from the viewpoint of the simplicity of the synthesis of the dihalogen body or monohalogen body of the unit B.

Next, an organic light emitting device of the present invention will be described in detail.

The organic light emitting device of the present invention includes at least: a pair of electrodes; and one or more layers each containing an organic compound, the one or more layers being interposed between the pair of electrodes. In the organic light emitting device, at least one layer of the one or more layers each containing an organic compound contains at least one kind of the above-mentioned compound of the present invention.

The at least one layer of the one or more layers each containing an organic compound is preferably a light emitting layer.

Figure 3:
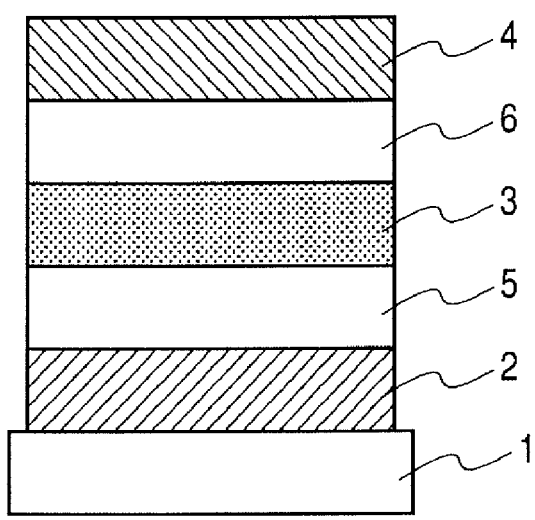
FIG. 3 is a sectional view showing an example of an organic light emitting device in the present invention.

FIG. 3 illustrates a preferable example of the organic light emitting device of the present invention.

FIG. 3 illustrates the organic light emitting device having a structure in which the anode 2, the hole transporting layer 5, the light emitting layer 3, the electron transporting layer 6, and the cathode 4 are provided on a substrate 1 in the stated order. The organic layers including the light emitting layer are positioned between the anode and the cathode. One kind of the fluoranthene compound of the present invention is included in the organic layers. More specifically, the fluoranthene compound is included in the light emitting layer.

The organic light emitting device illustrated in FIG. 3 has separate carrier-transporting function and light emitting function. The light emitting device is used in combination with compounds each having hole-transporting property, electron-transporting property, or light emitting property as appropriate, thereby allowing a significant increase in freedom of choice in material to be used. Various compounds having different light emission wavelengths can be used, thereby allowing an increase in variety of light emission hue. Further, luminous efficiency can be improved by efficiently trapping each carrier or exciton in the light emitting layer 3 provided in the middle of the device. FIG. 3 is a sectional view illustrating an example of the organic light emitting device according to the present invention.

As an example other than FIG. 3, there is an organic light emitting device having a structure in which the anode 2, the light emitting layer 3, and the cathode 4 are provided on the substrate 1 in the stated order. As the light emitting device used here, a compound having all of hole-transporting property, electron-transporting property, and light emitting property, or compounds having the respective properties used in combination, is/are useful.

Further, in a case of the organic light emitting device having a structure in which the anode 2, the hole transporting layer 5, the electron transporting layer 6, and the cathode 4 are provided on the substrate 1 in the stated order, a light emitting substance whose material has at least one of hole-transporting property and electron-transporting property is used for any one of the layers. It is useful to use the light emitting substance in combination with a non-illuminant hole-transporting substance or electron-transporting substance. In this case, the light emitting layer is formed of the hole transporting layer 5 or the electron transporting layer 6.

Another structure is also provided in which the hole-injecting layer is inserted into a side of the anode 2 of the organic light emitting device of FIG. 3. This structure is effective for improving adhesiveness between the anode 2 and the hole transporting layer 5 or for improving hole-injecting property, which is effective in lowering a voltage to be applied to the device.

Further, another structure is provided in which a layer (the hole/exciton-blocking layer) for blocking travel of a hole or exciton to a side of the cathode 4 is inserted between the light emitting layer 3 and the electron transporting layer 6 of the organic light emitting device of FIG. 3. The structure uses a compound having an extremely high ionization potential for the hole/exciton-blocking layer, which is effective for improving luminous efficiency.

Note that, the structures described above and illustrated in FIG. 3 represent a basic device structure, and the structure of the organic light emitting device using the compound of the present invention is not limited to those structures. For example, the organic light emitting device of the present invention may have any one of various layer structures including: a structure having an insulating layer provided at an interface between the electrode and the organic layer; a structure having an adhesive or interference layer; and a structure in which a hole transporting layer is composed of two layers with different ionization potentials.

The organic light emitting device of the present invention can be used in any one of the device structures described above and illustrated in FIG. 3.

In particular, an organic layer using the compound of the present invention is useful as a light emitting layer, an electron transporting layer, or a hole transporting layer. In addition, a layer formed by a vacuum vapor deposition method or a solution coating method is hardly crystallized and has excellent stability over time.

In the present invention, the compound of the present invention is used particularly as a component of the light emitting layer. However, a conventionally known low-molecular-weight-based or polymer-based hole transportable compound, luminescent compound, or electron transportable compound can be used together as required.

Examples of the compounds are shown below.

A preferred hole-injection transporting material has excellent mobility for facilitating injection of a hole from an anode and for transporting the injected hole to a light emitting layer. Examples of a low-molecular-weight-based or polymer-based material having hole-injection transporting property include, but are not limited to: a triarylamine derivative; a phenylenediamine derivative; a triazole derivative; an oxadiazole derivative; an imidazole derivative; a pyrazoline derivative; a pyrazolone derivative; an oxazole derivative; a fluorenone derivative; a hydrazone derivative; a stilbene derivative; a phthalocyanine derivative; a porphyrin derivative; poly(vinylcarbazole); poly(silylene); poly(thiophene); and other conductive polymers.

Examples of a usable material which is mainly involved in a light emitting function except the compound to be used in the organic light emitting device of the present invention include, but are not limited to: a fused ring aromatic compound (including a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, or rubrene); a quinacridone derivative; an acridone derivative; a coumarin derivative; a pyran derivative; Nile red; a pyrazine derivative; a benzoimidazole derivative; a benzothiazole derivative; a benzoxazole derivative; a stilbene derivative; an organometallic complex (including: an organic aluminum complex such as tris(8-quinolinolato)aluminum; or an organic beryllium complex); and a polymer derivative (including a poly(phenylene vinylene)derivative, a poly(fluorene) derivative, a poly(phenylene) derivative, a poly(thienylene vinylene)derivative, or a poly(acetylene) derivative).

The electron-injection transporting material can be arbitrarily selected from materials which facilitate injection of an electron from a cathode and which have a function of transporting the injected electron to a light emitting layer. The material is selected in consideration of, for example, the balance with the mobility of a carrier of the hole transporting material. Examples of a material having electron-injection transporting property include, but are not limited to, an oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative, and an organometallic complex.

In the organic light emitting device according to the present invention, the layer containing the compound of the present invention and layers containing other organic compounds are each formed by the following method. A thin film is generally formed by a vacuum vapor deposition method, an ionized vapor deposition method, sputtering, plasma, or a known coating method (such as a spin coating, dipping, casting, LB, or ink jet method) in which a compound is dissolved in an appropriate solvent. In film formation by a coating method, in particular, a film can be formed by using a compound in combination with an appropriate binder resin.

The binder resin can be selected from a wide variety of binder resins. Examples of the binder resin include, but not limited to: a polyvinyl carbazole resin; a polycarbonate resin; a polyester resin; a polyallylate resin; a polystyrene resin; an ABS resin; a polybutadine resin; a polyurethane resin; an acrylic resin; a methacrylic resin; a butyral resin; a polyvinyl acetal resin; a polyamide resin; a polyimide resin; a polyethylene resin; a polyethersulfone resin; a diallyl phthalate resin; a phenol resin; an epoxy resin; a silicone resin; a polysulfone resin; and a urea resin. One kind of binder resin may be used alone, or two or more kinds thereof may be mixed and used as a copolymer. Further, an additive such as a known plasticizer, antioxidant, or ultraviolet absorber may be used in combination as required.

An anode material preferably has as large a work function as possible, and examples thereof include: a metal element such as gold, platinum, silver, copper, nickel, palladium, cobalt, selenium, vanadium, or tungsten; an alloy thereof; and a metal oxide such as tin oxide, zinc oxide, indium oxide, indium tin oxide (ITO), or indium zinc oxide. Further, a conductive polymer such as polyaniline, polypyrrole, polythiophene, or polyphenylene sulfide can also be used. Each of those electrode materials may be used alone, or two or more kinds thereof may be used in combination. Further, the anode can have a single layer structure or a multilayer structure.

Meanwhile, a cathode material preferably has a small work function, and examples thereof include: a metal element such as lithium, sodium, potassium, calcium, magnesium, aluminum, indium, ruthenium, titanium, manganese, yttrium, silver, lead, tin, or chromium; and an alloy thereof such as a lithium-indium alloy, a sodium-potassium alloy, a magnesium-silver alloy, an aluminum-lithium alloy, an aluminum-magnesium alloy, or a magnesium-indium alloy. A metal oxide such as indium tin oxide (ITO) can also be used. Each of those electrode materials may be used alone, or two or more kinds thereof may be used in combination. Further, the cathode can have a single layer structure or a multilayer structure.

At least one of the anodes and the cathodes may be semitransparent.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate. In addition, the substrate can have a color filter film, a fluorescent color converting filter film, a dielectric reflection film, or the like for controlling luminescent color.

Further, a protective layer or a sealing layer can be formed on the produced device to prevent contact between the device and oxygen or moisture. Examples of the protective layer include: a diamond thin film; a film formed of an inorganic material such as metal oxide or metal nitride; a polymer film formed of a fluorine resin, polyparaxylene, polyethylene, a silicone resin, and a polystyrene resin; and a photo-curable resin. Further, the device itself can be covered with glass, an airtight film or a metal and packaged with an appropriate sealing resin.

The device of the present invention can be produced by producing a thin film transistor (TFT) on a substrate, and then connecting the device to the TFT.

Regarding the light extraction direction of a device, the device can have a bottom emission structure (structure in which light is extracted from a substrate side) or a top emission structure (structure in which light is extracted from an opposite side of the substrate).

In addition, one characteristic of the present invention is that a light emitting region contains the fluoranthene compound of the present invention as a guest material and a host material. A compound having a fused ring hydrocarbon skeleton which is tetracyclic or more is a particularly excellent host material, and examples of the fused ring hydrocarbon skeleton which is tetracyclic or more include a pyrene skeleton, a fluoranthene skeleton, a benzofluoranthene skeleton, a tetracene skeleton, a triphenylene skeleton, and a chrysene skeleton.

Examples of a compound having a pyrene skeleton among such skeletons include, but not limited to, the following materials.

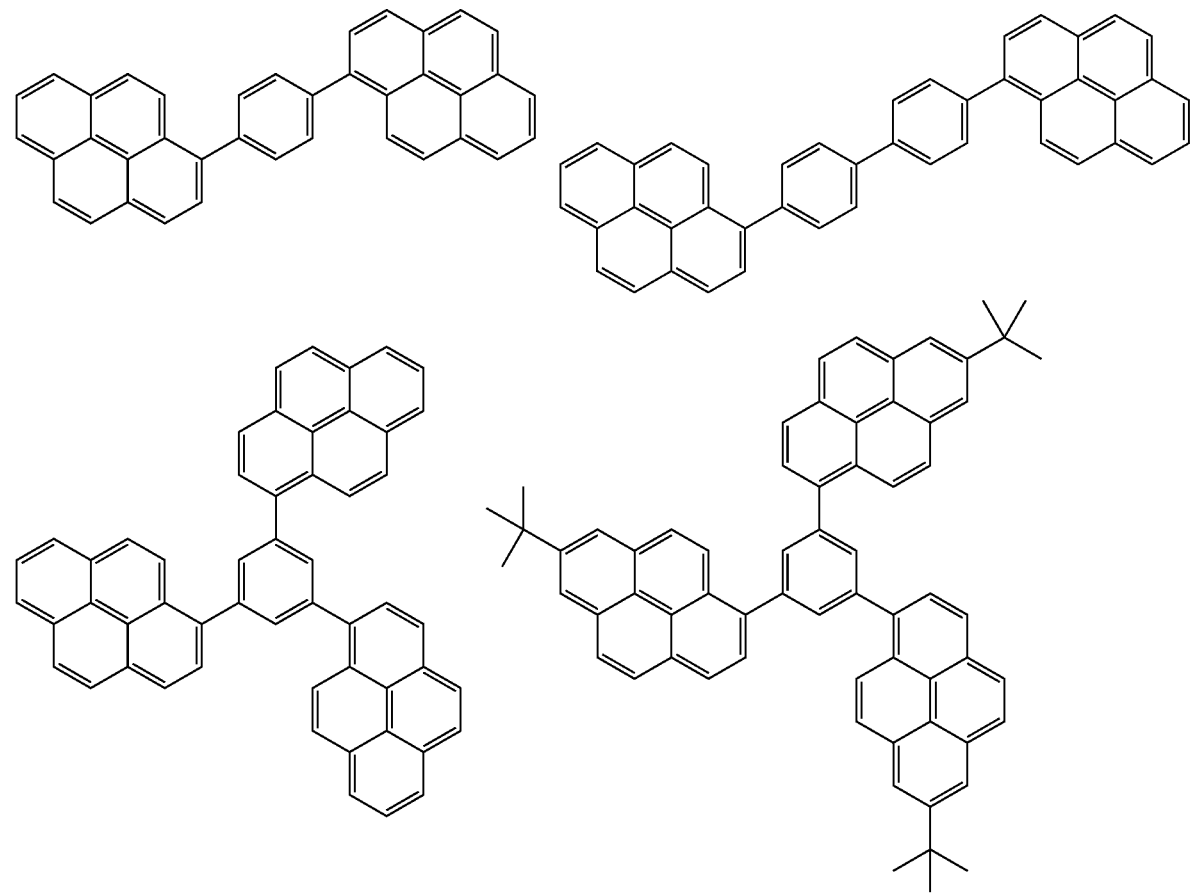

-continued
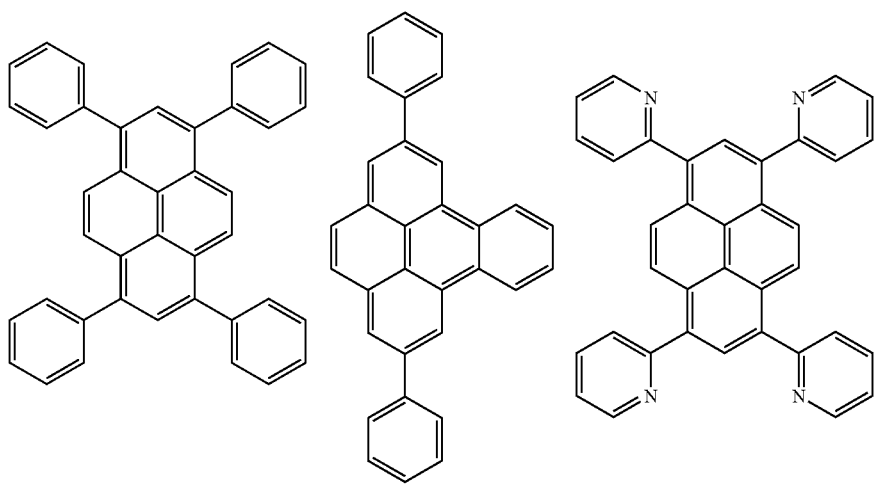
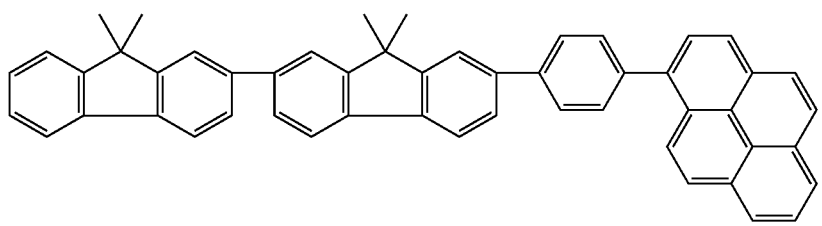
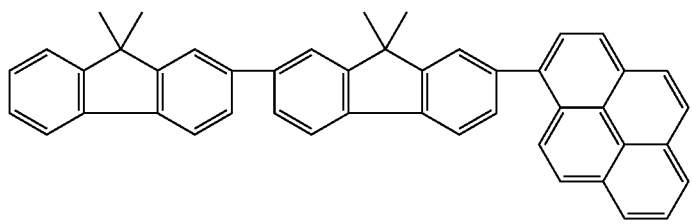
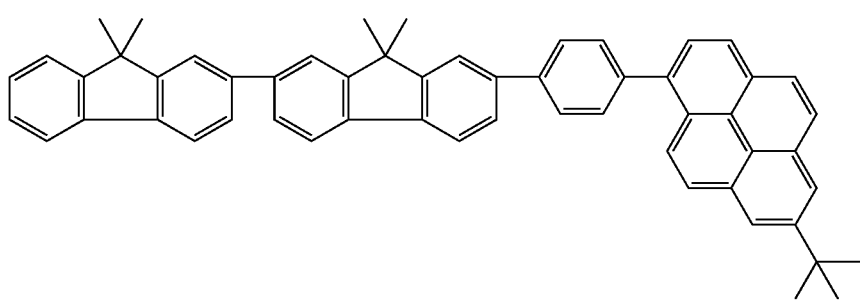
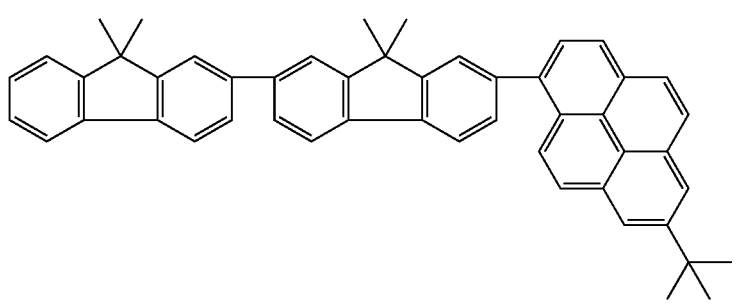

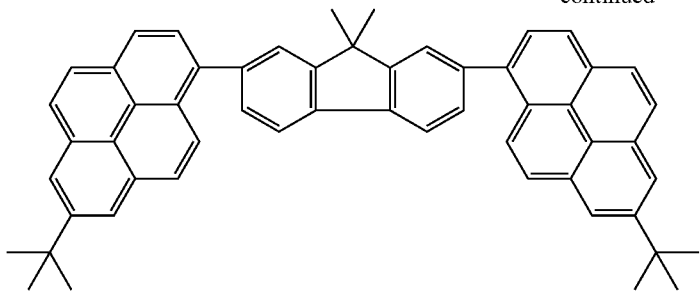

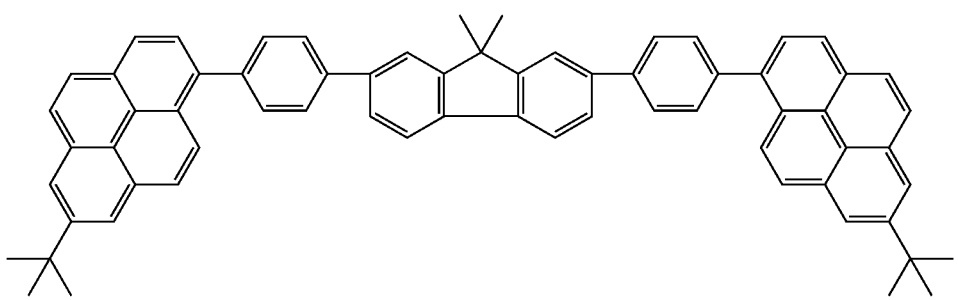

Hereinafter, the present invention will be described more specifically by way of examples, but the present invention is not limited to the examples.

EXAMPLE 1

Method of Producing Exemplified Compound No. 101

Exemplified Compound No. 101 of the present invention can be produced by, for example, the method to be described below.

(1) Synthesis of 9-(7-tert-butyl-3-methylpyren-1-yl)anthracene as Intermediate Compound 1

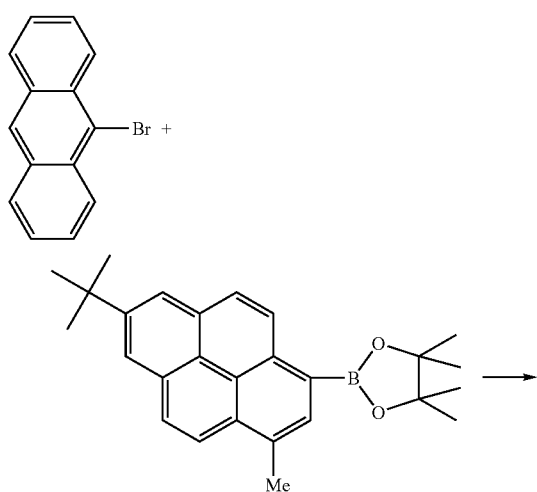

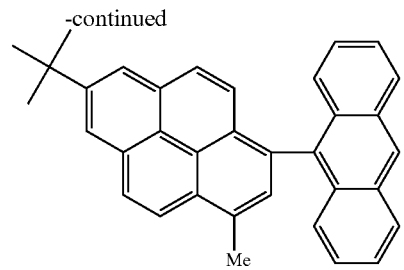

Compound 1

Under a nitrogen atmosphere, 5 g (19.4 mmol) of 9-bromoanthracene and 7.73 g (19.4 mmol) of 2-(7-tert-butyl-3-methylpyren-1-yl)-4,4,5,5-tetramethyl-[1,3,2]dioxaborolane were dissolved in a mixed solvent of toluene (240 ml) and ethanol (120 ml). Further, an aqueous solution prepared by dissolving 3.93 g (38.8 mmol) of sodium carbonate in 40 ml of distilled water was added to the resultant, and the whole was stirred at 50° C. for 30 minutes. Tetrakis(triphenylphosphine)palladium (1.57 g, 1.36 mmol) was added to the resultant, and the whole was stirred under heat on a silicone oil bath heated to 90° C. for 3.5 hours. After the resultant had been cooled to room temperature, water, toluene, and ethyl acetate were added to the resultant to separate an organic layer. Further, a water layer was extracted with a mixed solvent of toluene and ethyl acetate (twice), and was then added to the solution of the organic layer that had been separated first. The organic layer was washed with a saturated salt solution, and was then dried with sodium sulfate. The solvent was removed by distillation, and the residue was purified by means of silica gel column chromatography (toluene:heptane 1:3), whereby 6.5 g of Intermediate Compound 1 were obtained.

(2) Synthesis of 9-bromo-10-(7-tert-butyl-3-methylpyren-1-yl)anthracene as Intermediate Compound 2

Compound 1 ⟶

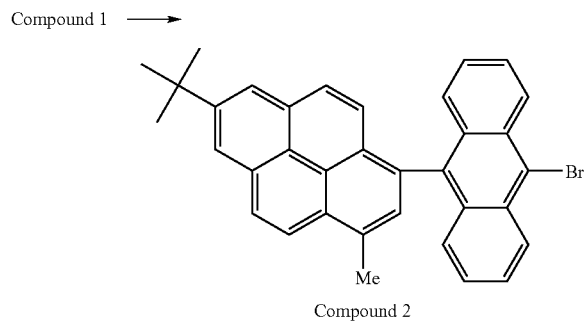

Compound 2

Under a nitrogen atmosphere, Intermediate Compound 1 (6 g, 13.4 mmol) was dissolved in 100 ml of dioxane. An aqueous solution prepared by dissolving 0.75 g (13.4 mmol) of potassium hydroxide in 5 ml of distilled water was added to the solution, and 2.56 g (16.1 mmol) of bromine were dropped to the mixture. After the resultant had been stirred on an oil bath heated to 40° C. for 30 minutes, 9.7 g (3.08 mmol) of a 5% sodium thiosulfate solution were added to the resultant, and the whole was stirred at 20° C. for an additional 2 hours. After having been filtrated, the resultant was washed with methanol and recrystallized from toluene (twice). The resultant was dried in a vacuum under heat, whereby 3.6 g of Intermediate Compound 2 were obtained.

(3) Synthesis of Exemplified Compound No. 101

Compound 2 +

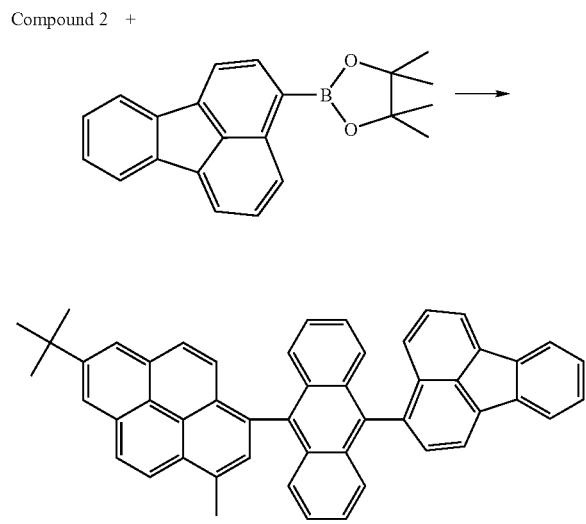

Under a nitrogen atmosphere, Intermediate Compound 2 (3 g, 5.69 mmol) and 1.87 g (5.69 mmol) of fluoranthen-3-yl-4,4,5,5-tetramethyl-[1,3,2]dioxaborolane were dissolved in a mixed solvent of toluene (200 ml) and ethanol (100 ml). Further, an aqueous solution prepared by dissolving 0.64 g (11.4 mmol) of sodium carbonate in 30 ml of distilled water was added to the resultant, and the whole was stirred at 50° C. for 30 minutes. Tetrakis(triphenylphosphine)palladium (0.66 g, 0.571 mmol) was added to the resultant, and the whole was stirred under heat on a silicone oil bath heated to 90° C. for 5 hours. After the resultant had been cooled to room temperature, water, toluene, and ethyl acetate were added to the resultant to separate an organic layer. Further, a water layer was extracted with a mixed solvent of toluene and ethyl acetate (twice), and was then added to the solution of the organic layer that had been separated first. The organic layer was washed with a saturated salt solution, and was then dried with sodium sulfate. The solvent was removed by distillation, and the residue was purified by means of silica gel column chromatography (mobile phase; toluene:heptane=1:3). The resultant was dried at 120° C. in a vacuum, and, furthermore, was subjected to sublimation purification, whereby 2.3 g of Exemplified Compound No. 101 as a pale yellow solid were obtained.

Matrix assisted laser desorption/ionization time-of-flight mass spectrometry (MALDI-TOF MS) confirmed 648.4 as the M+ of the compound (no matrix).

Further, NMR measurement identified the structure of the compound (FIG. 1).

The glass transition temperature of the compound in a glass state was measured with a DSC (Pyris 1) manufactured by PerkinElmer by increasing the temperature of the compound from room temperature at a rate of temperature increase of 10° C./min. As a result, the glass transition temperature of the compound was 216° C.

Figure 2:
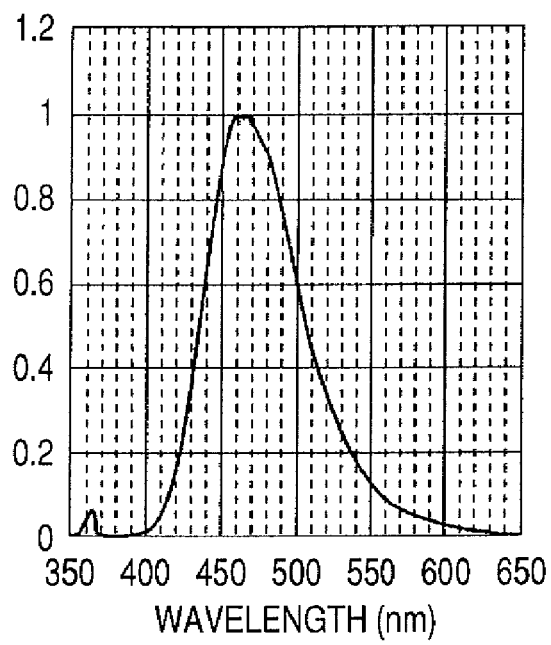
FIG. 2 is a view showing the PL spectrum of a mixed film produced from a chloroform solution containing 5 wt % of Exemplified Compound No. 101 with respect to Compound 5 as a host material by a spin coating method.

A mixed film was produced from a chloroform solution containing 5 wt % of Exemplified Compound No. 101 with respect to Compound 5 shown below as a host material, and the PL spectrum of the film was measured. As a result, a spectrum derived from Exemplified Compound No. 101 was observed (FIG. 2).

EXAMPLE 2

An organic light emitting device having the structure illustrated in FIG. 3 was produced by the method described below.

First reference numerals of FIG. 3 will be described. There are provided a substrate 1, an anode 2, a light emitting layer 3, a cathode 4, a hole transporting layer 5, and an electron transporting layer 6.

Indium tin oxide (ITO) as the anode 2 was formed as a film having a thickness of 120 nm on a glass substrate as the substrate 1 by a sputtering method, and the resultant was used as a transparent conductive supporting substrate. The resultant substrate was subjected to ultrasonic cleaning in acetone and isopropyl alcohol (IPA) in the stated order. Then, the substrate was washed in boiling IPA and dried. The substrate was further subjected to UV/ozone cleaning to be used as a transparent conductive supporting substrate.

A chloroform solution containing 0.2 wt % was prepared by using Compound 3 represented by the following structural formula as a hole transporting material.

Compound 3

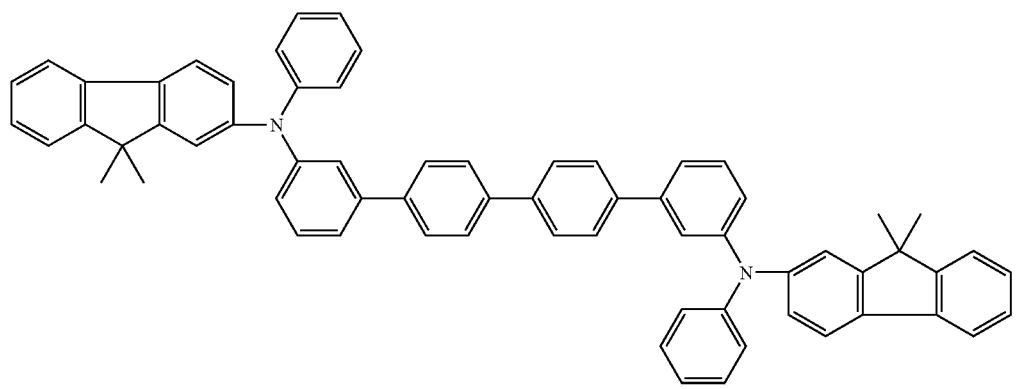

This solution was dropped onto the above-mentioned ITO electrode and formed into a film on the ITO electrode through spin coating at a revolving speed of 500 rpm for 10 seconds at first and then at a revolving speed of 1,000 rpm for 1 minute. Then, the whole was placed in a vacuum oven at 80° C. and dried for 10 minutes, to thereby completely remove the solvent in the thin film. The thus-formed hole transporting layer 5 had a thickness of 15 nm.

Next, as the light emitting layer 3, Exemplified Compound No. 101 described above as a first compound and Compound 4 represented by the following structural formula as a below-mentioned second compound were co-deposited from the vapor on the hole transporting layer 5. The resultant light emitting layer 3 had a thickness of 25 nm. A degree of vacuum during vapor deposition was $1.0 \times 10^{-4}$ Pa and a film formation rate during vapor deposition was 0.2 nm/second or more to 0.3 nm/second or less.

Compound 4

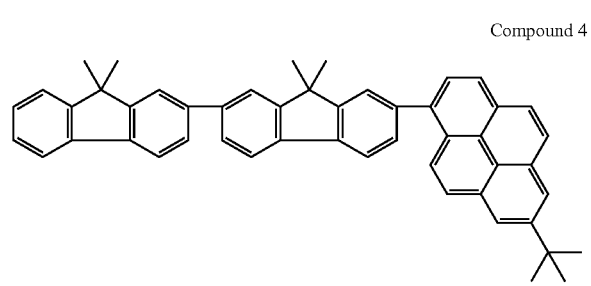

Further, as the electron transporting layer 6, 2,9-[2-(9,9'-dimethylfluorenyl)]-1,10-phenanthroline was formed into a film having a thickness of 25 nm through a vacuum vapor deposition method. A degree of vacuum during vapor deposition was $1.0 \times 10^{-4}$ Pa and a film formation rate during vapor deposition was 0.2 nm/second or more to 0.3 nm/second or less.

Next, lithium fluoride (LiF) was formed into a film having a thickness of 0.5 nm on the above-mentioned organic layer by a vacuum vapor deposition method, and an aluminum film having a thickness of 100 nm was formed thereon through a vacuum vapor deposition method, to thereby produce an electron-injection electrode (cathode 4). As a result, an organic light emitting device with the electron-injection electrode (cathode 4) was produced. A degree of vacuum during deposition was $1.0 \times 10^{-4}$ Pa. According to the condition of formation, a lithium fluoride film formation rate was 0.05 nm/second, and an aluminum film formation rate was 1.0 nm/second or more to 1.2 nm/second or less.

The obtained organic EL device was covered with a protective glass and sealed with an acrylic resin binder in a dry air atmosphere to prevent degradation of the device due to adsorption of moisture thereon.

Under application of a voltage of 4 V to the thus-obtained device having the ITO electrode (anode 2) as a positive electrode and the Al electrode (cathode 4) as a negative electrode, blue light emission with a luminous efficiency of 3.8 lm/W was observed. The CIE chromaticity was x=0.15, y=0.14, and blue light with good color purity was emitted and observed.

Further, a voltage was applied to the device under a nitrogen atmosphere for 100 hours. As a result, the device was observed to emit light with good property continuously.

EXAMPLE 3

A device was produced in the same manner as in Example 2 except that Compound 5 represented by the following structural formula was used instead of Compound 4 of Example 2. The device of this example was observed to emit light with a luminous efficiency of 4 lm/W at an applied voltage of 4 V. In addition, the device was observed to emit blue light having CIE chromaticity coordinates (x, y) of (0.15, 0.14) and a good color purity.

Further, a voltage was applied to the device under a nitrogen atmosphere for 100 hours. As a result, the device was observed to emit good light continuously.

Compound 5

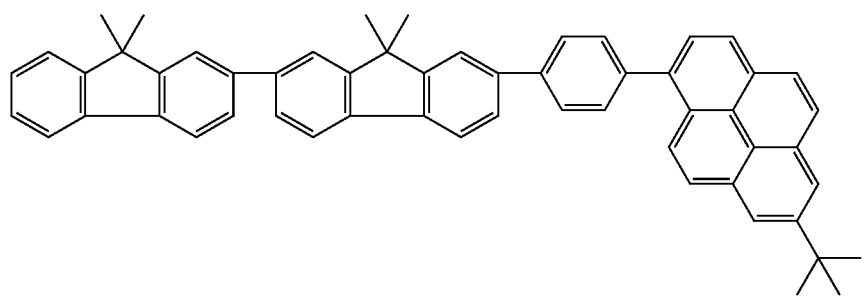

EXAMPLE 4

Synthesis of Exemplified Compound No. 111

Exemplified Compound No. 111 can be synthesized in the same manner as in Example 1 except that 5,8-di-tert-butylfluoranthen-3-yl-4,4,5,5-tetramethyl-[1,3,2]dioxaborolane is used instead of fluoranthen-3-yl-4,4,5,5-tetramethyl-[1,3,2]dioxaborolane of Example 1.

EXAMPLE 5

Synthesis of Exemplified Compound No. 115

Exemplified Compound No. 115 can be synthesized in the same manner as in Example 1 except that fluoranthen-8-yl-4,4,5,5-tetramethyl-[1,3,2]dioxaborolane is used instead of fluoranthen-3-yl-4,4,5,5-tetramethyl-[1,3,2]dioxaborolane of Example 1.

EXAMPLE 6

Synthesis of Exemplified Compound No. 103

Exemplified Compound No. 103 can be synthesized in the same manner as in Example 1 except that 2-(7-iso-propyl-3-methylpyren-1-yl)-4,4,5,5-tetramethyl-[1,3,2]dioxaborolane is used instead of 2-(7-tert-butyl-3-methylpyren-1-yl)-4,4,5,5-tetramethyl-[1,3,2]dioxaborolane of Example 1.

EXAMPLE 7

Synthesis of Exemplified Compound No. 105

Exemplified Compound No. 105 can be synthesized in the same manner as in Example 1 except that 2-(2,7-di-tert-3-butylpyren-4-yl)-4,4,5,5-tetramethyl-[1,3,2]dioxaborolane is used instead of 2-(7-tert-butyl-3-methylpyren-1-yl)-4,4,5,5-tetramethyl-[1,3,2]dioxaborolane of Example 1.

EXAMPLE 8

Synthesis of Exemplified Compound No. 116

(1) Synthesis of 1-bromo-4-(7-tert-butylpyren-1-yl)naphthalene as Intermediate Compound 7

Intermediate Compound 7 can be synthesized in the same manner as in the synthesis of Intermediate Compound 1 of Example 1 except that: 1,4-dibromonaphthalene is used instead of 9-bromoanthracene used in the synthesis of Intermediate Compound 1 of Example 1; 2-(7-tert-butylpyren-1-yl)-4,4,5,5-tetramethyl-[1,3,2]dioxaborolane is used instead of 2-(7-tert-butyl-3-methylpyren-1-yl)-4,4,5,5-tetramethyl-[1,3,2]dioxaborolane used in the synthesis of Intermediate Compound 1 of Example 1; and a solution of 2-(7-tert-butylpyren-1-yl)-4,4,5,5-tetramethyl-[1,3,2]dioxaborolane in the mixture of toluene and ethanol is dropped to the mixed solution of 1,4-dibromonaphthalene, an aqueous solution of sodium carbonate, and tetrakis(triphenylphosphine)palladium.

(2) Synthesis of Exemplified Compound No. 116

Exemplified Compound No. 116 can be synthesized in the same manner as in Example 1 except that 1-bromo-4-(7-tert-butylpyren-1-yl)naphthalene is used instead of 9-bromo-10-(7-tert-butyl-3-methylpyren-1-yl)anthracene used in the synthesis of Exemplified Compound No. 101 of Example 1.

EXAMPLE 9

Synthesis of Exemplified Compound No. 121

Exemplified Compound No. 121 can be synthesized in the same manner as in Example 8 except that 1,5-dibromonaphthalene is used instead of 1,4-dibromonaphthalene of Example 8.

EXAMPLE 10

Synthesis of Exemplified Compound No. 124

Exemplified Compound No. 124 can be synthesized in the same manner as in Example 8 except that 1,5-dibromo-3,7-dimethylnaphthalene is used instead of 1,4-dibromonaphthalene of Example 8.

EXAMPLE 11

Synthesis of Exemplified Compound No. 129

Exemplified Compound No. 129 can be synthesized in the same manner as in Example 8 except that 6,12-dibromochrysene is used instead of 1,4-dibromonaphthalene of Example 8.

EXAMPLE 12

Synthesis of Exemplified Compound No. 139

Exemplified Compound No. 139 can be synthesized in the same manner as in Example 1 except that 9-bromo-10-(naphthalen-1-yl)anthracene obtained by causing 1 equivalent of 2-(naphthalen-1-yl)-4,4,5,5-tetramethyl-[1,3,2]dioxaborolane to react with 9,10-dibromoanthracene under the conditions of a Suzuki coupling reaction identical to those of the synthesis of Intermediate Compound 7 of Example 8 is used instead of 9-bromo-10-(7-tert-butyl-3-methylpyren-1-yl)anthracene.

EXAMPLE 13

Synthesis of Exemplified Compound No. 144

Exemplified Compound No. 144 can be synthesized in the same manner as in Example 12 except that 2-(phenanthren-3-yl)-4,4,5,5-tetramethyl-[1,3,2]dioxaborolane is used instead of 2-(naphthalen-1-yl)-4,4,5,5-tetramethyl-[1,3,2]dioxaborolane of Example 12.

EXAMPLE 14

Synthesis of Exemplified Compound No. 153

Exemplified Compound No. 153 can be synthesized in the same manner as in Example 12 except that 2-(chrysene-6-yl)-4,4,5,5-tetramethyl-[1,3,2]dioxaborolane is used instead of 2-(naphthalen-1-yl)-4,4,5,5-tetramethyl-[1,3,2]dioxaborolane of Example 12.

EXAMPLE 15

This application claims the benefit of Japanese Patent Application No. 2006-116903, filed Apr. 20, 2006, and Japanese Patent Application No. 2007-040901, filed Feb. 21, 2007, which are hereby incorporated by reference herein in their entirety.

The invention claimed is:

1. An organic light emitting device comprising:
a pair of electrodes; and
an organic compound layer interposed between the pair of electrodes,
wherein the organic compound layer is a light emitting layer which comprises a host material and a guest material, and
wherein the guest material is a compound of formula (2):

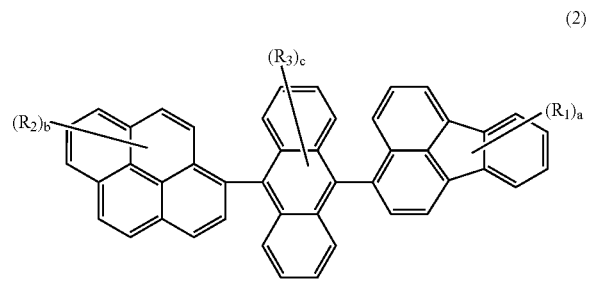

(2)

where $R_1$, $R_2$, and $R_3$ each represent a group selected from the group consisting of a hydrogen atom, a halogen atom, a substituted or unsubstituted alkyl group, a substituted or unsubstituted aralkyl group, a substituted or unsubstituted alkoxy group, a substituted or unsubstituted aryl group, and a substituted or unsubstituted heterocyclic group, $R_1$'s are identical to or different from each other, $R_2$'s are identical to or different from each other, $R_3$'s are identical to or different from each other, and $R_1$, $R_2$, and $R_3$ are identical to or different from one another, a and b each represent an integer of 1 to 9, and c represents an integer of 1 to 8; and wherein the host material is selected from the group consisting of:

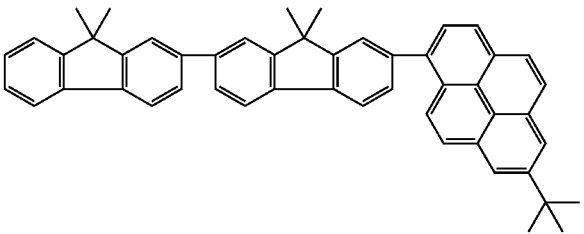

and

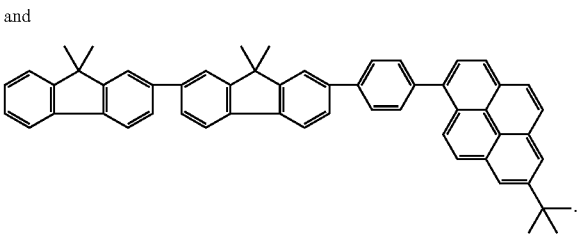

2. The organic light emitting device according to claim 1, wherein the guest material is the compound represented by the following formula:

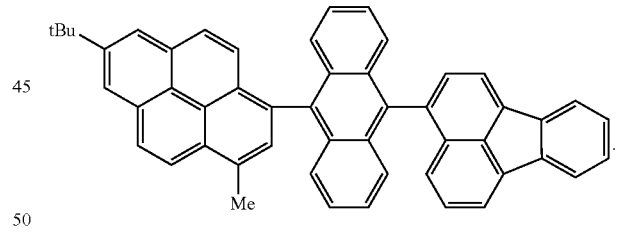

* * * * *